United States Patent
Lewis et al.

(10) Patent No.: US 9,969,746 B2
(45) Date of Patent: May 15, 2018

(54) OPIOID COMPOUNDS AND THEIR USES

(71) Applicants: THE UNIVERSITY OF BATH, Bath (GB); THE TORREY PINES INSTITUTE FOR MOLECULAR STUDIES, Port St. Lucie, FL (US); SRI INTERNATIONAL, Menlo Park, CA (US)

(72) Inventors: John Lewis, Bath and North East Somerset (GB); Stephen Husbands, Bath and North East Somerset (GB); Lawrence Toll, Port St. Lucie, FL (US)

(73) Assignee: The University of Bath, Bath (GB)

(*) Notice: Subject to any disclaimer, the term of this patent is extended or adjusted under 35 U.S.C. 154(b) by 3 days.

(21) Appl. No.: 15/102,066

(22) PCT Filed: Dec. 5, 2014

(86) PCT No.: PCT/GB2014/053615
§ 371 (c)(1),
(2) Date: Jun. 6, 2016

(87) PCT Pub. No.: WO2015/082932
PCT Pub. Date: Jun. 11, 2015

(65) Prior Publication Data
US 2016/0304529 A1   Oct. 20, 2016

Related U.S. Application Data

(60) Provisional application No. 61/912,169, filed on Dec. 5, 2013.

(51) Int. Cl.
*C07D 489/08* (2006.01)
*C07D 489/02* (2006.01)

(52) U.S. Cl.
CPC ......... *C07D 489/08* (2013.01); *C07D 489/02* (2013.01)

(58) Field of Classification Search
None
See application file for complete search history.

(56) References Cited

U.S. PATENT DOCUMENTS

| | | | |
|---|---|---|---|
| 3,828,050 A | 8/1974 | Buckett et al. | |
| 4,241,066 A | 12/1980 | Kobylecki et al. | |
| 4,241,067 A | 12/1980 | Kobylecki et al. | |
| 4,925,848 A | 5/1990 | Lewis et al. | |
| 5,849,731 A | 12/1998 | Nagase et al. | |
| 5,886,001 A | 3/1999 | Schmidhammer | |
| 6,136,817 A | 10/2000 | Schmidhammer | |
| 6,291,470 B1 | 9/2001 | Nagase et al. | |
| 6,323,212 B1 | 11/2001 | Nagase et al. | |
| 7,285,665 B2 | 10/2007 | Cantrell et al. | |
| 7,655,671 B2 | 2/2010 | Schmidhammer et al. | |
| 7,838,677 B2 | 11/2010 | Wang et al. | |
| 7,999,104 B2 | 8/2011 | Carroll et al. | |
| 7,999,105 B2 | 8/2011 | Wang et al. | |
| 8,227,609 B2 | 7/2012 | Weigl et al. | |
| 8,236,957 B2 | 8/2012 | Rezaie et al. | |
| 8,318,937 B2 | 11/2012 | Mitchell et al. | |
| 8,436,174 B2 | 5/2013 | Cantrell et al. | |
| 8,563,724 B2 | 10/2013 | Grote et al. | |
| 8,563,727 B2 | 10/2013 | Cantrell et al. | |
| 8,669,366 B2 | 3/2014 | Wang et al. | |
| 8,691,768 B2 | 4/2014 | Fields et al. | |

(Continued)

FOREIGN PATENT DOCUMENTS

| | | |
|---|---|---|
| CN | 1050130 C | 3/2000 |
| WO | WO 03/070191 A1 | 8/2003 |

(Continued)

OTHER PUBLICATIONS

Lambert, DG. et al. simultaneously targeting of multiple opioid receptors: a strategy to improve side-effect profile. British Journal of Anaesthesia. 2009, vol. 103, p. 38.*
Goodman, AJ. et al. Mu Opioid Receptor Antagonists: Recent Developments. ChemMedChem. 2007, vol. 2, p. 1552.*
Schmitz, C. et al. Hippocampal Neuron Loss Exceeds Amyloid Plaque Load in a Transgenic Mouse Model of Alzheimer's Disease. American Journal of Pathology. 2004, vol. 164, p. 1495.*
Al-Hasani, R. and Bruchas, M.R., "Molecular Mechanisms of Opioid Receptor-Dependent Signaling and Behavior," *Anesthesiology* 115:1363-1381, Lippincott Williams & Wilkins (2011).
Aschenbach, L., "Selective Non-Peptide Mu-Opioid Receptor Antagonist: Design, Synthesis and Biological Studies," *VCU Theses and Dissertations*, Paper 1610, VCU Scholars Compass, Virginia Commonwealth University (2008).

(Continued)

*Primary Examiner* — Taofiq A Solola
(74) *Attorney, Agent, or Firm* — Sterne, Kessler, Goldstein & Fox P.L.L.C.

(57) ABSTRACT

The present invention relates to opioid compounds, especially to C14 esters and ethers of naltrexone and analogs thereof. The present invention also relates to compositions, methods and medical uses that employ such compounds. More specifically, the present invention pertains to compounds of formula: and to their use in the treatment of diseases and disorders including pain, hyperalgesia, addiction, substance abuse disorders, stress, anorexia, anxiety, depression, cough, asthma, hypertension, gastrointestinal motility disorder, water retention, cognitive disorders, and locomotor disorders.

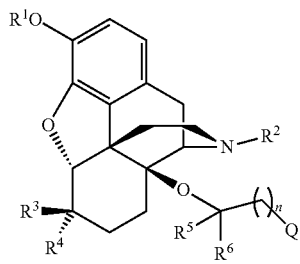

23 Claims, 2 Drawing Sheets

(56) References Cited

U.S. PATENT DOCUMENTS

| | | | |
|---|---|---|---|
| 8,710,226 B2 | 4/2014 | Patel et al. | |
| 8,772,308 B2 | 7/2014 | Zhang et al. | |
| 8,980,908 B2 | 3/2015 | Zhang et al. | |
| 2004/0033253 A1* | 2/2004 | Shevchuk | A61K 9/7084 424/449 |
| 2004/0180036 A1 | 9/2004 | Ashton et al. | |
| 2006/0063792 A1 | 3/2006 | Dolle et al. | |
| 2008/0176884 A1* | 7/2008 | Perez | C07D 489/08 514/282 |
| 2008/0207669 A1 | 8/2008 | Perez et al. | |
| 2008/0234306 A1 | 9/2008 | Perez et al. | |
| 2008/0318905 A1 | 12/2008 | Muhammad et al. | |
| 2009/0047279 A1 | 2/2009 | Perez et al. | |
| 2009/0054651 A1 | 2/2009 | Eipert et al. | |
| 2009/0192095 A1 | 7/2009 | Franklin et al. | |
| 2011/0136845 A1 | 6/2011 | Trawick et al. | |
| 2011/0251229 A1 | 10/2011 | Watkins et al. | |
| 2012/0046272 A1 | 2/2012 | Sesha | |
| 2012/0258981 A1 | 10/2012 | Duncan | |
| 2012/0270847 A1 | 10/2012 | Franklin et al. | |
| 2013/0102780 A1 | 4/2013 | Giguere et al. | |
| 2013/0102784 A1 | 4/2013 | Reisch et al. | |
| 2013/0231485 A1 | 9/2013 | Tamura et al. | |
| 2013/0281698 A1 | 10/2013 | Schuetz et al. | |
| 2014/0371255 A1 | 12/2014 | Zhang et al. | |

FOREIGN PATENT DOCUMENTS

| | | |
|---|---|---|
| WO | WO 2009/067275 A1 | 5/2009 |
| WO | WO 2009/132313 A2 | 10/2009 |
| WO | WO 2010/083384 A2 | 7/2010 |
| WO | WO 2010/112942 A1 | 10/2010 |
| WO | WO 2011/009015 A1 | 1/2011 |
| WO | WO 2012/025213 A2 | 3/2012 |
| WO | WO 2012/054566 A2 | 4/2012 |
| WO | WO 2014/170704 A1 | 10/2014 |
| WO | WO 2014/172478 A1 | 10/2014 |

OTHER PUBLICATIONS

BMCS 7th Postgraduate Symposium, Wolfson Lecture Theatre, Department of Chemistry, University of Cambridge, United Kingdom, 34 pages, Royal Society of Chemistry (Dec. 13, 2013).

Cami-Kobeci, G. et al., "BU10038 as a potential new analgesic with reduced side effect profile," Poster Presentation, National Institute on Drug Abuse, The Science of Drug Abuse & Addiction, University of Bath, United Kingdom, one page (2014).

Cami-Kobeci, G. et al., "Naltrexone esters as a new therapeutic treatment for drug abuse," Poster Presentation, National Institute on Drug Abuse, The Science of Drug Abuse & Addiction, University of Bath, United Kingdom (Dec. 13, 2013).

Cami-Kobeci, G. et al., "Mixed κ/μ Opioid Receptor Agonists: The 6β-Naltrexamines," *J. Med. Chem.* 52:1546-1552, American Chemical Society (2009).

Cami-Kobeci, G. et al., "Structural determinants of opioid and NOP receptor activity in derivatives of buprenorphine," *J. Med. Chem.* 54:6531-6537, American Chemical Society (2011).

Casal-Dominguez, J.J. et al., "In vivo and in vitro characterization of naltrindole-derived ligands at the κ-opioid receptor," *J. Psychopharmacol.* 27:192-202, Oxford University Press (Feb. 2013).

Dietis, N. et al., "Simultaneous targeting of multiple opioid receptors: a strategy to improve side-effect profile," *Br. J. Anaesth.* 103:38-49, Oxford University Press (2009).

Ding, H. et al., "Bifunctional MOP/NOP receptor agonist, BU10038, as a strong and safe analgesic in monkeys," *J. Pain* 16:S59, abstract No. 332, Churchill Livingstone, Philadelphia (2015).

9th European Opioid Conference, Programme and Abstracts, 66 pages, Guildford, United Kingdom, Pain Research Forum (Apr. 10-12, 2013).

Ghirmai, S. et. al., "Synthesis and pharmacological evaluation of 6-naltrexamine analogs for alcohol cessation," *Bioorg. Med. Chem.* 17:6671-6681, Pergamon Press (2009).

Greedy, B.M. et al., "Orvinols with Mixed Kappa/Mu Opioid Receptor Agonist Activity," *J. Med. Chem.* 56:3207-3216, American Chemical Society (Feb. 25, 2013).

Greiner, E. et al., "Synthesis and Biological Evaluation of 14-Alkoxymorphians. 18. N-Substituted 14-Phenylpropyloxymorphinan-6-ones with Unanticipated Agonist Properties: Extending the Scope of Common Structure-Activity Relationships," *J. Med. Chem.* 46:1758-1763, American Chemical Society (2003).

Jenck, F. et al., "A synthetic agonist at the orphanin FQ/nociceptin receptor ORL1: Anxiolytic profile in the rat," *PNAS* 97:4938-4943, National Academy of Sciences (2000).

Jordan, B.A. et al., "Opioids and Their Complicated Receptor Complexes," *Neuropsychopharmacology* 23:S5-S18, American College of Neuropsychopharmacology (2000).

Khroyan, T.V. et al., "BU08073 a buprenorphine analog with partial agonist activity at mu receptors in vitro but long-lasting opioid antagonist activity in vivo in mice," *Br. J. Pharmacol.* 172:668-680, The British Pharmacological Society (2015).

Khroyan T.V. et al., "The First Universal Opioid Ligand, (2S)-2-[5R, 6R, 7R, 14S)-N-cyclopropylmethyl-4,5,epoxy-6,14-ethano-3-hydroxy-6-methoxymorphinan-7-yl]-3,3-dimethylpentan-2-ol (BU08028): Characterization of the In Vitro Profile and in Vivo Behavioral Effects in Mouse Models of Acute Pain and Cocaine-Induced Reward," *J. Pharmacol. Exp. Ther.* 336:952-961, The American Society for Pharmacology and Experimental Therapeutics (2011).

Ko, M.-C. and Husbands, S.M., "Effects of Atypical κ-Opioid Receptor Agonists on Intrathecal Morphine-Induced Itch and Analgesia in Primates," *J. Pharmacol. Exp. Ther.* 328:193-200, The American Society for Pharmacology and Experimental Therapeutics (2009).

Moynihan, H. et al., "14β-O-Cinnamoylnaltrexone and Related Dihydrocodeinones are Mu Opioid Receptor Partial Agonists with Predominant Antagonist Activity," *J. Med. Chem.* 52:1553-1557, American Chemical Society (2009).

Moynihan, H.A. et al., "Fumaroylamino-4,5-epoxymorphinans and Related Opioids with Irreversible μ Opioid Receptor Antagonist Effects," *J. Med. Chem.* 55:9868-9874, American Chemical Society (2012).

Nieland, N.P.R. et al.,"14β-Arylpropiolylamino-17-cyclopropylmethyl-7,8-dihydronormorphinones and related opioids. Further examples of pseudo-irreversible mu opioid receptor antagonists," *J. Med. Chem.* 52:6926-6930, American Chemical Society (2009).

Nieland, N.P.R. et al., "14β-Cinnamoylamidomorphinones and Codeinones. Analogs of the Selective Irreversible Antagonist Clocinnamox," *Analgesia* 1:611-614, Cognizant Communication Corporation (1995).

Nieland, N.P.R. et al., "Structural Determinants of Opioid Activity in Derivatives of 14-Aminomorphinones: Effect of Substitution in the Aromatic Ring of Cinnamoylaminomorphinones and codeinones," *J. Med. Chem.* 49:5333-5338, American Chemical Society (2006).

Rennison, D. et al., "Cinnamoyl Derivatives of 7α-Aminomethyl-6,14-endoethanotetrahydrothebaine and 7α-Aminomethyl-6,14-endoethanotetrahydroripavine and Related Opioid Ligands," *J. Med. Chem.* 18:5176-5182, American Chemical Society (2007).

Rennison, D. et al., "Structural Determinants of Opioid Activity in Derivatives of 14-Aminomorphinones: Effects of Changes to the Chain Linking the $C_{14}$-Amino Group to the Aryl Ring," *J. Med. Chem.* 49:6104-6110, American Chemical Society (2006).

Schmidhammer, H. and Spetea, M., "Synthesis of 14-Alkoxymorphinan Derivatives and Their Pharmacological Actions," *Top. Curr. Chem.* 128:2010-2077, Springer-Verlag, Germany (2010).

Spagnolo, B. et al., "Activities of mixed NOP and μ-opioid receptor ligands," *Br. J. Pharmacol.* 153:609-619, Nature Publishing Group (2008).

(56) References Cited

OTHER PUBLICATIONS

Stavitskaya, L. and Coop, A., "Most recent developments and modifications of 14-alkylamino and 14-alkoxy-4,5-epoxymorphinan derivatives," *Mini Rev. Med. Chem.* 11:1002-1008, Bentham Science Publishers, Netherlands (2011).
Stavitskaya, L., "Phenylpropyloxyethylamines: Opioids lacking a tyrosine mimetic," Dissertation directed by Coop, A., submitted to the faculty of the Graduate School of the University of Maryland, Baltimore (2011).
Stinchcomb, A.L. et al., "Straight-Chain Naltrexone Ester Prodrugs: Diffusion and Concurrent Esterase Biotransformation in Human Skin," *J. Pharm. Sci.* 91:2571-2578, Wiley-Liss, Inc. (2002).
Toll, L. et al., "Pharmacology of Mixed NOP/Mu Ligands," ACS Symposium Series vol. 1131, Research and Development of Opioid-Related Ligands, Ko, M.-C. and Husbands, S.M., eds., Ch. 17, pp. 369-391, American Chemical Society (May 10, 2013).
Yuan, Y. et al., "Design, Synthesis, and Biological Evaluation of 14-Heteroaromatic-Substittued Naltrexone Derivatives: Pharmacological Profile Switch from Mu Opioid Receptor Selectivity to Mu/Kappa Opioid Receptor Dual Selectivity," *J. Med. Chem.* 56: 9156-9169, American Chemical Society (Oct. 21, 2013).
Zhang, Y. et al., "Opioid receptor selectivity profile change via isosterism for 14-O-substituted naltrexone derivatives," *Bioorg. Med. Chem. Letts.* 23:3719-3722, Elsevier Ltd. (May 16, 2013).
International Search Report for International Patent Appl. No. PCT/GB2014/053615, European Patent Office, Rijswijk, Netherlands, dated Feb. 17, 2015.
Written Opinion of the International Searching Authority for International Patent Appl. No. PCT/GB2014/053615, European Patent Office, Munich, Germany, dated Feb. 17, 2015.
International Preliminary Report on Patentability for International Patent Appl. No. PCT/GB2014/053615, The International Bureau of WIPO, Geneva, Switzerland, dated Jun. 7, 2016.
Database Registry, Chemical Abstracts Service, XP002735367, Accession No. 759395-35-2, United States (2004).
Data Registry, Chemical Abstracts Service, XP002735368, Accession No. 30964-43-3, United States (1984).
Database Registry, Chemical Abstracts Service, XP002735369, Accession No. 30964-38-6, United States (1984).
Database Registry, Chemical Abstract Service, XP002735370, Accession No. 30964-34-2, United States (1984).
Grant Renewal Application for Federal Assistance from National Institutes of Health (Form SF 424) (Tracking No. GRANT00528869) for University of Bath, Federal Identifier: DA007315, Catalog of Federal Domestic Assistance No. 93.279, Title: Discovery of New Treatments for Drug Abuse (Oct. 2008).

\* cited by examiner

OPIOID COMPOUNDS AND THEIR USES

This invention was made with US government support under DA07315, DA020469 and DA023281 awarded by NIH. The government has certain rights in the invention.

FIELD OF THE INVENTION

The present invention relates to opioid compounds, especially to C14 esters and ethers of naltrexone and analogues thereof. The present invention also relates to compositions, methods and medical uses that employ such compounds.

BACKGROUND OF THE INVENTION

There are three classical opioid receptors, mu (MOP), delta (DOP) and kappa (KOP), which play important physiological and pharmacological roles, especially in pain regulation. Morphine, the prototype MOP agonist, remains the "Gold Standard" for clinical analgesia. The predominant unwanted effects of MOP agonists are their reinforcing effects, which lead to abuse and physical dependence. These effects are important for another major use of MOP agonists—the treatment of opiate abuse and dependence as less dangerous heroin substitutes on which addicts can be stabilized before detoxification.

In 1994, a fourth member of the GPCR family of opioid receptors was discovered, followed soon after by the isolation of its endogenous ligand, nociceptin. Though sharing a high degree of amino acid homology with the classical opioid receptors, affinity for the nociceptin (NOP) receptor among clinical opioids has been shown only in the case of buprenorphine. NOP ligands have been shown to have antidepressant activity, antianxiety effects and the ability to modulate MOP agonist-induced development of tolerance and physical dependence when MOPr and NOPr agonists are co-administered. (Whiteside and Kyle, 2013) (Mustazza and Bastanzio, 2011).

Despite substantial research investment in the field by several pharmaceutical companies, to date no NOP selective ligand has progressed through to clinical practice. Recent research activity has been focused on bifunctional MOP/NOP agonist ligands based on the hypothesis that since NOP agonists block development of tolerance and physical dependence to MOP agonism, ligands having both NOP and MOP agonism should maintain analgesic activity but show less tolerance and addiction liability. Design strategies have started from leads with MOP or NOP agonist selectivity onto which the alternative affinity/efficacy is grafted. KOP antagonists have been shown in preclinical and clinical studies to have potential as antidepressants and for the prevention of relapse in recovering cocaine addicts. For example, the KOPr antagonists norBNI and JDTic have been shown to block stress-induced potentiation of cocaine place preference (McLaughlin et al, 2003) and to block footshock-induced reinstatement of cocaine self-administration behaviour (Beardsley et al, 2005; Redila and Chavkin, 2008). KOPr antagonists have also been shown, in rats, to selectively attenuate ethanol-dependent self-administration while leaving nondependent ethanol self-administration unaffected (Walker and Koob, 2008). This appears consistent with earlier findings of a decrease in alcohol self-administration in KOR knockout mice (Kovacs et al, 2005). KOP receptor antagonists have also demonstrated efficacy in various models of stress related psychiatric illnesses including anxiety, depressive disorders, and addiction (Van't Veer and Carlezon Jr, 2013).

MOP antagonism in agents lacking any MOP agonism (zero efficacy), exemplified by naltrexone (1a), nalmefene (1c), β-naltrexol (1b) and desoxonaltrexone (1d) has given rise to clinical use of 1a and 1c for the treatment of alcohol abuse and dependence and for the prevention of relapse in detoxified opiate addicts. These ligands display little or no affinity for NOP receptors.

SUMMARY OF THE INVENTION

The present invention is based on the discovery that certain predominantly MOP antagonist 14-hydroxyepoxymorphinan derivatives (naltrexone (1a), nalmefene (1c), 1-naltrexol (1b) and desoxonaltrexone (1d)) which have no measurable affinity for the NOP receptor can be converted into derivatives by acylation or alkylation of the 14-hydroxyl group into ligands having substantial affinity for NOP. Since this is achieved whilst the new ligands retain high affinity for the classical opioid receptors, their potential as analgesics with very low abuse liability or as relapse prevention agents for recovering opioid, cocaine and alcohol addicts and as treatments for depression, is markedly enhanced.

The present invention concerns C14 esters and ethers of naltrexone, naltrexol (β- and α-naltrexol), desoxonaltrexone and nalmefene, especially arylalkanoyl "esters" and arylalkyl "ethers", having substantial affinity for NOP receptors and preferably significant efficacy for these receptors. The most useful compounds of the invention also have low or very low efficacy at MOPr and KOPr with higher efficacy at NOPr. Those with very low efficacy at MOP and KOP with some agonist effect at NOP (e.g. 1e) may be useful as agents to prevent relapse in recovering opiate, cocaine and alcohol abusers and addicts and also as antidepressants. Those compounds of the invention with high affinity and substantial efficacy for NOP together with modest MOP efficacy and low efficacy for KOP (e.g. 1f) offer promise as analgesics with very low abuse potential, lower than that of buprenorphine particularly as treatments for neuropathic pain and hyperalgesia. They may be potential substitutes for buprenorphine as treatments for opiate abuse/addiction again having the advantage of lower abuse liability.

The present inventors have found that the region of space occupied by the t-butyl group of buprenorphine is key to good NOP receptor activity and have discovered that this region can also be accessed by certain acyl and alkyl groups attached to the C14-oxygen of antagonist ligands naltrexone, nalmefene, β-naltrexol, and desoxonaltrexone. This represents a novel method of introducing substantial NOPr affinity to these series that are known to show only negligible affinity for NOP receptors.

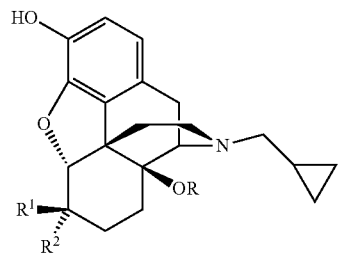

1

(a) R=H; $R^1$, $R^2$ is =O naltrexone
(b) R=H; $R^1$=OH, $R^2$=H β-naltrexol, (b') R=H; $R^1$=H, $R^2$=OH α-naltrexol
(c) R=H; $R^1$, $R^2$ is =$CH_2$ nalmefene
(d) R=$R^1$=$R^2$=H, desoxonaltrexone (e) $R^1$, $R^2$ is =O; R is $CO(CH_2)_2$-4-$CH_3OC_6H_4$ Example 12, Table 1
(f) $R^1$, $R^2$ is =O; R is $CO(CH_2)_2C_8H_5$ Example 11, Table 1
(g) $R^1$, $R^2$ is =O; R is $CO(CH_2)_3C_6H_5$ Example 27

Broadly the present invention relates to compounds of formula 2:

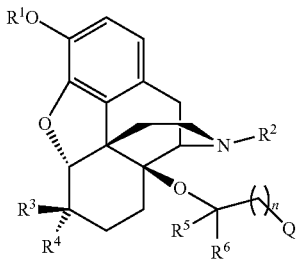

2 wherein
$R^1$ is H or methyl;
$R^2$ is $C_{3-5}$ alkyl, $C_{3-5}$ alkenyl or $C_{3-5}$ cycloalkyl-$C_{1-2}$alkyl;
$R^3$ and $R^4$ are together =O or =$CH_2$, or one is H and the other is OH, or both are H;
$R^5$ and $R^6$ are together =O or both are H;
n is 1-4; and
Q is branched alkyl of 3-6 carbon atoms or branched alkenyl of 3-6 carbon atoms, phenyl or heteroaryl of 5-6 ring atoms with at least one atom selected from N, O or S;
  wherein each phenyl or heteroaryl is optionally substituted with one or two $R^Q$ substituents, wherein each $R^Q$ is independently selected from halogen, $C_{1-3}$alkyl, $CF_3$, OH, $C_{1-3}$alkyloxy, —$NH_2$, —$NHR^7$, or $NR^7R^8$, wherein $R^7$ and $R^8$ are independently $C_{1-3}$alkyl; or two adjacent $R^Q$ together form a —O—$(CH_2)_m$—O— moiety, wherein m is 1, 2 or 3;
and to pharmaceutically acceptable salts, hydrates, and/or solvates thereof.

In a first aspect, the present invention provides a compound of formula 2:

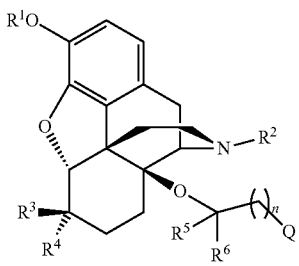

2 wherein
$R^1$ is H or methyl;
$R^2$ is $C_{3-5}$alkyl, $C_{3-5}$alkenyl or $C_{3-5}$ cycloalkyl-$C_{1-2}$alkyl;
$R^3$ and $R^4$ are together =O or =$CH_2$ or one is H and the other is OH, or both are H;
$R^5$ and $R^6$ are together =O or both are H;
n is 1-4; and Q is branched alkyl of 3-6 carbon atoms or branched alkenyl of 3-6 carbon atoms, phenyl, or heteroaryl of 5-6 ring atoms with at least one atom selected from N, O or S;

wherein each phenyl or heteroaryl is optionally substituted with one or two $R^Q$ substituents, wherein each $R^Q$ is independently selected from halogen, $C_{1-3}$alkyl, $CF_3$, OH, $C_{1-3}$alkyloxy, —$NH_2$, —$NHR^7$, or $NR^7R^8$, wherein $R^7$ and $R^8$ are independently $C_{1-3}$alkyl; or two adjacent $R^Q$ together form a —O—$(CH_2)_m$—O— moiety, wherein m is 1, 2 or 3;

with the proviso that:
when $R^3$ and $R^4$ are =O or =$CH_2$, $R^5$ and $R^6$ are =O and n is 1, Q is not unsubstituted phenyl, and when $R^3$ and $R^4$ are =O, $R^5$ and $R^6$ are not H;

or a pharmaceutically acceptable salt, hydrate, and/or solvate thereof.

In some embodiments, $R^5$ and $R^6$ are together =O.

$R^3$ and $R^4$ may together be =O. That is, the compound may be an ester of naltrexone.

According, the compound may be a compound of formula 3:

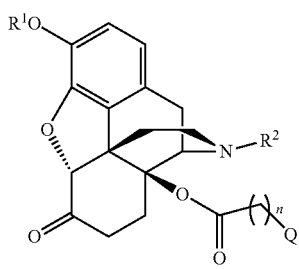

3 wherein
$R^1$ is H or methyl;
$R^2$ is $C_{3-5}$alkyl, $C_{3-5}$alkenyl or $C_{3-5}$cycloalkyl-$C_{1-2}$alkyl;
n is 1-4; and Q is branched alkyl of 3-6 carbon atoms or branched alkenyl of 3-6 carbon atoms, phenyl, or heteroaryl of 5-6 ring atoms with at least one atom selected from N, O or S;

wherein each phenyl or heteroaryl is optionally substituted with one or two $R^Q$ substituents, wherein each $R^Q$ is independently selected from halogen, $C_{1-3}$alkyl, $CF_3$, OH, $C_{1-3}$alkyloxy, —$NH_2$, —$NHR^7$, or $NR^7R^8$, wherein $R^7$ and $R^8$ are independently $C_{1-3}$alkyl; or two adjacent $R^Q$ together form a —O—$(CH_2)_m$—O— moiety, wherein m is 1, 2 or 3;

with the proviso that when n is 1, Q is not unsubstituted phenyl.

Alternatively, one of $R^3$ and $R^4$ may be H and the other may be OH, that is, the compound may be an ester of naltrexol. The compound may be either epimer of naltrexol (α and β), or a mixture of both. Preferably, the compound is either α-naltrexol or β-naltrexol in diasteroerically enriched, preferably substantially enantiopure (>95% ee), form.

Accordingly, the compound may be a compound of formulae 4 or 4', formula 4' being the C6 epimer of formula 4, or be provided as a diastereomeric mixture:

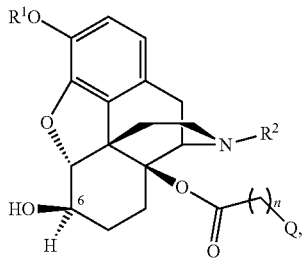

(4': alternative (α) epimer at C6)

wherein
R¹ is H or methyl;
R² is $C_{3-5}$alkyl, $C_{3-5}$alkenyl or $C_{3-5}$cycloalkyl-$C_{1-2}$alkyl;
n is 1-4; and
Q is branched alkyl of 3-6 carbon atoms or branched alkenyl of 3-6 carbon atoms, phenyl, or heteroaryl of 5-6 ring atoms with at least one atom selected from N, O or S;
  wherein each phenyl or heteroaryl is optionally substituted with one or two $R^Q$ substituents, wherein each $R^Q$ is independently selected from halogen, $C_{1-3}$alkyl, $CF_3$, OH, $C_{1-3}$alkyloxy, —$NH_2$, —$NHR^7$, or $NR^7R^8$, wherein $R^7$ and $R^8$ are independently $C_{1-3}$alkyl; or two adjacent $R^Q$ together form a —O—$(CH_2)_m$—O— moiety, wherein m is 1, 2 or 3.

R³ and R⁴ may together be =CH₂. That is, the compound may be an ester of nalmefene.

According, the compound may be a compound of formula 5:

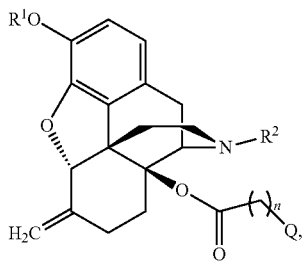

wherein
R¹ is H or methyl;
R² is $C_{3-5}$alkyl, $C_{3-5}$alkenyl or $C_{3-5}$cycloalkyl-$C_{1-2}$alkyl;
n is 1-4; and
Q is branched alkyl of 3-6 carbon atoms or branched alkenyl of 3-6 carbon atoms, phenyl, or heteroaryl of 5-6 ring atoms with at least one atom selected from N, O or S;
  wherein each phenyl or heteroaryl is optionally substituted with one or two $R^Q$ substituents, wherein each $R^Q$ is independently selected from halogen, $C_{1-3}$alkyl, $CF_3$, OH, $C_{1-3}$alkyloxy, —$NH_2$, —$NHR^7$, or $NR^7R^8$, wherein $R^7$ and $R^8$ are independently $C_{1-3}$alkyl; or two adjacent $R^Q$ together form a —O—$(CH_2)_m$—O— moiety, wherein m is 1, 2 or 3;
with the proviso that when n is 1, Q is not unsubstituted phenyl.

R³ and R⁴ may both be H. That is, the compound may be an ester of desoxonaltrexone.

Accordingly, the compound may be a compound of formula 6:

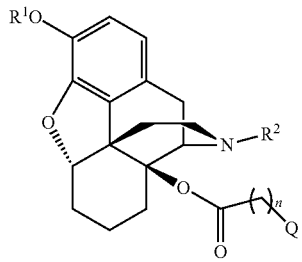

wherein
R¹ is H or methyl;
R² is $C_{3-5}$alkyl, $C_{3-5}$alkenyl or $C_{3-5}$cycloalkyl-$C_{1-2}$alkyl;
n is 1-4; and
Q is branched alkyl of 3-6 carbon atoms or branched alkenyl of 3-6 carbon atoms, phenyl, or heteroaryl of 5-6 ring atoms with at least one atom selected from N, O or S;
  wherein each phenyl or heteroaryl is optionally substituted with one or two $R^Q$ substituents, wherein each $R^Q$ is independently selected from halogen, $C_{1-3}$alkyl, $CF_3$, OH, $C_{1-3}$alkyloxy, —$NH_2$, —$NHR^7$, or $NR^7R^8$, wherein $R^7$ and $R^8$ are independently $C_{1-3}$alkyl; or two adjacent $R^Q$ together form a —O—$(CH_2)_m$—O— moiety, wherein m is 1, 2 or 3.

In other embodiments, $R^8$ and $R^6$ are both H, that is, the compounds are C14-O ethers.

One of R³ and R⁴ may be H and the other may be OH, that is, the compound may be an ether of naltrexol. The compound may be either epimer of naltrexol (α and β), or a mixture of both. Preferably, the compound is either α-naltrexol or β-naltrexol in diastereoerically enriched, preferably substantially enantiopure (>95% ee), form.

Accordingly, the compound may be a compound of formulae 7 or 7', formula 7' being the C6 epimer of formula 7, or be provided as a diastereomeric mixture:

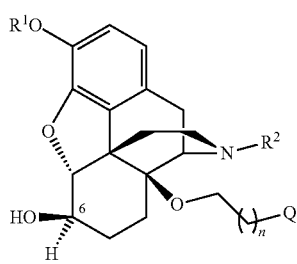

(7': alternative (α) epimer at C6)

wherein
R² is H or methyl;
R² is $C_{3-5}$alkyl, $C_{3-5}$alkenyl or $C_{3-5}$ cycloalkyl-$C_{1-2}$alkyl;
n is 1-4; and
Q is branched alkyl of 3-6 carbon atoms or branched alkenyl of 3-6 carbon atoms, phenyl, or heteroaryl of 5-6 ring atoms with at least one atom selected from N, O or S;
  wherein each phenyl or heteroaryl is optionally substituted with one or two $R^Q$ substituents, wherein each $R^Q$ is independently selected from halogen, $C_{1-3}$alkyl, $CF_3$, OH, $C_{1-3}$alkyloxy, —$NH_2$, —$NHR^7$, or $NR^7R^8$, wherein $R^7$ and $R^8$ are independently $C_{1-3}$alkyl; or two adjacent R$^Q$ together form a —O—(CH$_2$)$_m$—O— moiety, wherein m is 1, 2 or 3.

R$^3$ and R$^4$ may both be H. That is, the compound may be an ether of desoxonaltrexone.

Accordingly, the compound may be a compound of formula 8:

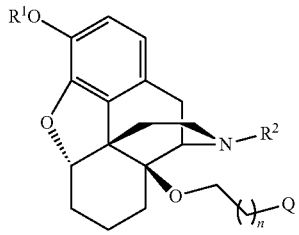

8 wherein
R$^1$ is H or methyl;
R$^2$ is C$_{3-5}$alkyl, C$_{3-5}$alkenyl or C$_{3-5}$cycloalkyl-C$_{1-2}$alkyl;
n is 1-4; and
Q is branched alkyl of 3-6 carbon atoms or branched alkenyl of 3-6 carbon atoms, phenyl, or heteroaryl of 5-6 ring atoms with at least one atom selected from N, O or S;
wherein each phenyl or heteroaryl is optionally substituted with one or two R$^Q$ substituents, wherein each R$^Q$ is independently selected from halogen, C$_{1-3}$alkyl, CF$_3$, OH, C$_{1-3}$alkyloxy, —NH$_2$, —NHR$^7$, or NR$^7$R$^8$, wherein R$^7$ and R$^8$ are independently C$_{1-3}$alkyl; or two adjacent R$^Q$ together form a —O—(CH$_2$)$_m$—O— moiety, wherein m is 1, 2 or 3.

R$^3$ and R$^4$ may together be =CH$_2$. That is, the compound may be an ether of nalmefene.

According, the compound may be a compound of formula 9:

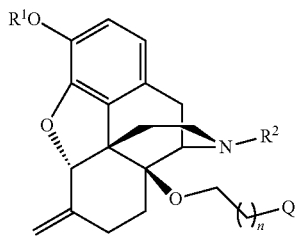

9 wherein
R$^1$ is H or methyl;
R$^2$ is C$_{3-5}$alkyl, C$_{3-5}$alkenyl or C$_{3-5}$cycloalkyl-C$_{1-2}$alkyl;
n is 1-4; and
Q is branched alkyl of 3-6 carbon atoms or branched alkenyl of 3-6 carbon atoms, phenyl, or heteroaryl of 5-6 ring atoms with at least one atom selected from N, O or S;
wherein each phenyl or heteroaryl is optionally substituted with one or two R$^Q$ substituents, wherein each R$^Q$ is independently selected from halogen, C$_{1-3}$alkyl, CF$_3$, OH, C$_{1-3}$alkyloxy, —NH$_2$, —NHR$^7$, or NR$^7$R$^8$, wherein R$^7$ and R$^8$ are independently C$_{1-3}$alkyl; or two adjacent R$^Q$ together form a —O—(CH$_2$)$_m$—O— moiety, wherein m is 1, 2 or 3.

In a further aspect, the present invention provides a method of modulating nociceptin receptor activity (NOP), the method comprising the step of contacting NOP with an effective amount of a compound of formula 2 as described herein.

The method may be in vitro or in vivo.

The modulation may be activation of NOP receptors in conjunction with MOP receptors or may be selective activation of NOP receptors combined with low, or no, agonist activity at MOP and KOP receptors; i.e. a profile of:

(i) MOP partial agonist/NOP receptor partial agonist and KOP antagonist activity; or (ii) MOP and KOP antagonist activity and NOP partial agonist activity.

The modulation may be in vitro or in vivo. The modulation may produce a pharmacological effect. Accordingly, the present invention further provides a method of producing a pharmacological effect in vivo, the method comprising contacting NOP receptor with an effective amount of a compound of formula 2 as described herein.

In some embodiments, the modulation is selective activation of NOP receptors with respect to mu opioid receptors (MOP) and kappa opioid receptors (KOP), the compound having significant NOP agonist activity combined with antagonist activity at MOP and KOP.

In other embodiments, the modulation is activation of NOP receptors combined with activation at mu opioid receptors (MOP), the compound having significant NOP agonist activity combined with low agonist activity at MOP and antagonist activity at kappa opioid receptors (KOP).

Significant NOP agonist activity, as used herein, refers to around 20% stimulation or higher of NOP receptors, relative to the standard agonist nociceptin.

In a further aspect, the present invention provides use of a compound of formula 2 as described herein in a method of treatment of the human or animal body by therapy.

The method may be for the treatment or prophylaxis of pain, especially neuropathic pain and hyperalgesia; opiate abuse and dependence. The method may be for the treatment of depression, anxiety, stress and the prevention of relapse to substance abuse, especially opiates, cocaine and alcohol.

The present invention further provides methods of treatment for diseases, conditions and disorders as described herein using compounds of formula 2 as described herein.

In any of the methods described herein, the compound may be a compound of formula 2 with the proviso that when R$^3$ and R$^4$ are =O or =CH$_2$, R$^5$ and R$^6$ are =O and n is 1, Q is not unsubstituted phenyl, and when R$^3$ and R$^4$ are =O, R$^5$ and R$^6$ are not H. In any of the methods described herein, the compound may be a compound of formula 2 according to any embodiment described herein.

DETAILED DESCRIPTION OF THE INVENTION

Figure 1A:
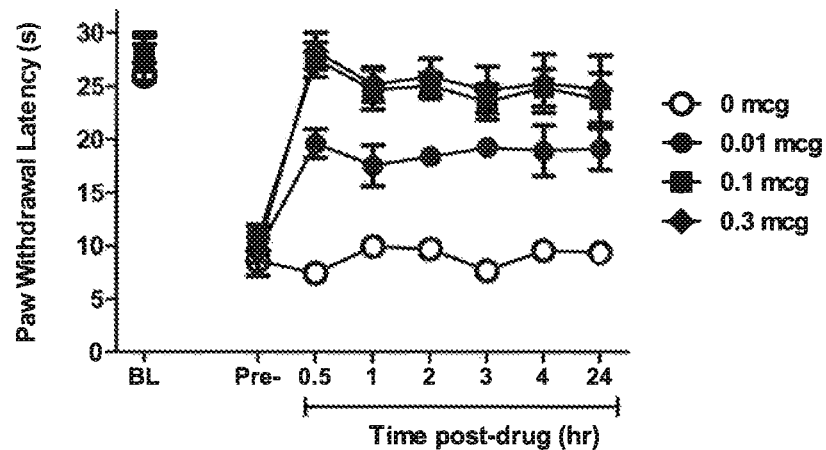
FIG. 1 shows the effect of intrathecal lion carrageenan-induced thermal hyperalgesia measured by paw withdrawal latency (FIG. 1a) and anti-hyperalgesic effect (FIG. 1b).

The following options and preferences apply independently and in any combination to all formulae described herein, except where such a combination is expressly prohibited or clearly impermissible.

The Group $R^1$ $R^1$ may be hydrogen or methyl. Preferably, $R^1$ is hydrogen.

The Group $R^2$

In compounds of the invention, $R^2$ may be selected from $C_{3-5}$alkyl, $C_{3-5}$alkenyl or $C_{3-5}$cycloalkyl-$C_{1-2}$alkyl.

Examples of $C_{3-5}$ alkyl include, but are not limited to, n-propyl, n-butyl, iso-butyl and iso-pentyl. Examples of $C_{3-5}$ alkenyl include, but are not limited to, allyl, methallyl ($CH_2C(CH_3)=CH_2$), crotyl ($CH_2CH=CHCH_3$) and dimethylallyl ($CH_2CH=C(CH_3)_2$). Examples of $C_{3-5}$cycloalkyl-$C_{1-2}$alkyl include, but are not limited to, cyclopropylmethyl and cyclobutylmethyl.

Preferably, $R^2$ is allyl or cyclopropylmethyl, most preferably cyclopropylmethyl.

The Group(s) $R^3$ and $R^4$ $R^3$ and $R^4$ may together be =O (naltrexone derivatives), may together be $CH_2$ (nalmefene derivatives), may both be H (desoxonaltrexone derivatives), or one may be H and the other OH (natrexol derivatives).

In some embodiments, $R^3$ and $R^4$ are together =O or $CH_2$, or one is H and the other is OH.

In some embodiments, $R^3$ and $R^4$ are together =O or $CH_2$.

In some embodiments, $R^3$ and $R^4$ are =O, or one is H and the other is OH.

Where one of $R^3$ and $R^4$ is H and the other is OH, preferably $R^3$ is H.

The Group(s) $R^5$ and $R^6$

The present invention relates to C6 esters ($R^5$ and $R^6$ together are =O) and ethers ($R^5$ and $R^6$ are both H).

In some embodiments, $R^5$ and $R^6$ together are =O. In other embodiments, $R^5$ and $R^6$ are both H.

The $(CH_2)$ n Chain n may be 1, 2, 3, or 4. Preferably, n is 1, 2, or 3, and n may, for example, be 1 or 2, or 2 or 3.

Most preferably, n is 2.

The Group Q

In some compounds of the invention, Q is phenyl or heteroaryl. Optionally, Q is substituted with one or two $R^Q$ groups.

In some preferred compounds, Q is a substituted phenyl. Q may be selected from 2,3-disubstituted phenyl, 2,4-disubstituted phenyl, 2,5-disubstituted phenyl, 2,6-disubstituted phenyl, 3,4-disubstituted phenyl, 3,5-disubstituted phenyl, 2-substituted phenyl, 3-substituted phenyl, or 4-substituted phenyl, wherein each substituent is an $R^Q$ substituent. In some preferred embodiments, Q is a mono-substituted phenyl.

In other preferred compounds, and as permitted herein, Q is unsubstituted phenyl.

In other preferred compounds, Q is heteroaryl optionally substituted by one or two $R^Q$ substituents. Heteroaryl as used herein refers to a five or six-membered aromatic ring comprising at least one heteroatom selected from N, O or S. Examples of heteroaryl groups include, but are not limited to, furanyl, pyrrolyl, thienyl, imidazoyl, pyrazolyl, triazolyl, tetrazolyl, oxazolyl, thiazolyl and isothiazolyl, pyridyl, pyrimidinyl, and piprazinyl.

In some compounds described herein, Q may be branched alkyl or branched alkenyl of 3-6 carbon atoms. Examples of branched $C_{3-6}$ alkyl include, but are not limited to, isopropyl ($CH(CH_3)_2$), isobutyl ($CH_2CH(CH_3)_2$), sec butyl ($CH(CH_3)CH_2CH_3$), isopentyl ($CH_2CH_2CH(CH_3)_2$), neopentyl ($CH_2C(CH_3)_3$) and neohexyl ($(CH_2)_2C(CH_3)_3$). Preferably, Q is branched alkyl, with isopropyl, isobutyl, and sec butyl being preferred.

It will be appreciated that compounds of the invention have the group —$(CR^5R^6)$—$(CH_2)$n-Q, that is, when Q is branched alkyl the branched alkyl is appended onto an alkyl chain. For example, when $R^5$ and $R^6$ together are =O, n=2 and is Q is isopropyl, the hydroxyl group is substituted by —(CO)—$CH_2CH_2CH(CH_3)_2$. Similarly, when $R^5$ and $R^6$ are both H, n=2 and is Q is isopropyl, the hydroxyl group is substituted by —$CH_2CH_2CH_2CH(CH_3)_2$.

The Group $R^Q$

Each $R^Q$ may be independently selected from halogen, $C_{1-3}$alkyl, $CF_3$, OH, $C_{1-3}$alkyloxy, —$NH_2$, —$NHR^7$, or $NR^7R^8$, wherein $R^7$ and $R^8$ are independently $C_{1-3}$alkyl; or two adjacent $R^Q$ together form a —O—$(CH_2)_m$—O— moiety, wherein m is 1, 2 or 3. Halogen as used herein refers to fluoro (F), chloro (Cl), bromo (Br), and iodo (I).

Preferably, each $R^Q$ is independently selected from halogen, $C_{1-3}$alkyl, $CF_3$, OH, or $C_{1-3}$alkyloxy, or two $R^Q$ together form a —O—$(CH_2)$—O— moiety.

More preferably, each $R^Q$ is independently selected from fluoro, chloro, methyl, $CF_3$, methoxy, or hydroxyl.

Some particularly preferred compounds of formula 2 are described below. The following preferences for the substituents present in the compounds may be present in any combination or permutation.

In some preferred compounds of formulae 3, 4, 4', 5 and 6 $R^1$ is H, $R^2$ is n-propyl, allyl, or cyclopropylmethyl, n is 1-3, Q is phenyl optionally mono- or di-substituted with halogen, methyl or methoxy groups except that in structures 3 and 5 when n is 1 the phenyl group is substituted with at least 1 substituent.

In some other preferred compounds of formulae 7, 7', 8 and 9 $R^1$ is H, $R^2$ is n-propyl, allyl, or cyclopropylmethyl, n is 2 and Q is phenyl optionally mono- or di-substituted with halogen, methyl or methoxy groups.

In an especially preferred compound of formula 3 $R^1$ is H, $R^2$ is cyclopropylmethyl, n is 2, and Q is phenyl.

Includes Other Forms:

Included in the above compound descriptions are salts, solvates and protected forms (including pro-drugs) of these substituents. For example a reference to an amino group includes the protonated form (—$N^+HR^1R^2$), a salt or solvate of the amino group, for example, a hydrochloride salt, as well as conventional protected forms of an amino group.

Similarly, a reference to a phenolic hydroxyl group also includes the anionic form (—O—), a salt or solvate thereof, as well as conventional protected forms of a hydroxyl group.

It may be convenient or desirable to prepare, purify, and/or handle a corresponding salt of the active compound, for example, a pharmaceutically-acceptable salt. Examples of pharmaceutically acceptable salts are discussed in Berge, et al., *J. Pharm. Sci.*, 66, 1-19 (1977).

It may be convenient or desirable to prepare, purify, and/or handle a corresponding solvate of the active compound. The term "solvate" is used herein in the conventional sense to refer to a complex of solute (e.g. active compound, salt of active compound) and solvent. If the solvent is water, the solvate may be conveniently referred to as a hydrate, for example, a mono-hydrate, a di-hydrate, a tri-hydrate, etc.

It may be convenient or desirable to prepare, purify, and/or handle the active compound in the form of a prodrug. The term "prodrug", as used herein, pertains to a compound which, when metabolised (e.g. in vivo), yields the desired active compound. Typically, the prodrug is inactive, or less active than the active compound, but may provide advantageous handling, administration, or metabolic properties.

For example, some prodrugs are labile esters of the active compound (e.g. a physiologically acceptable metabolically labile ester). During metabolism, the ester group (—C(=O) OR) is cleaved to yield the active drug. Such esters may be formed by esterification of the phenolic hydroxyl group.

Use of the Compounds of the Invention

The compounds of the present invention are pharmacologically active compounds, specifically active opioid and NOP receptor partial agonists/antagonists. Accordingly, the present invention is directed to compounds showing significant NOP activity, especially in combination with low or very low efficacy at mu and kappa opioid receptors.

The NOP receptor is a G-protein coupled receptor having significant homology with classical opioid receptors; however none of the endogenous opioid ligands show high affinity to NOP. The endogenous ligand for this receptor, nociceptin/orphanin FQ (N/OFQ) (Reinsceid et al. 1995), is a 17 amino acid peptide having sequence similarity to the opioid peptides, particularly dynorphin, but it itself does not have high affinity for other opioid receptors. Various studies have shown that the NOP receptor may play an important role in pain regulation (Mogil et al., 1996), the cardiovascular system (Gumusel et al., 1997), opioid tolerance (Ueda et al., 1997), learning and memory (Manabe 1998), anorexia (Pomois et al.), anxiety (Jenck et al., 1997), and others (Champion et al., 1997). Emerging pharmacological evidence suggests that NOP receptor agonists may be useful for the treatment of addiction, stress, anorexia, anxiety, cough, asthma and peripheral agonists may have utility in the treatment of hypertension, gastrointestinal motility disorder and water retention. Similarly NOP receptor antagonists (see, for example, Florin et al., 1996 and Goeldner et al. 2009) may be useful in enhancing cognitive function, and in the treatment of locomotor disorders and depression.

Preclinical and clinical data suggesting a role for KOP receptor antagonists in the treatment of various drugs of abuse and co-occurring psychiatric disorders. These studies include the ability of KOP antagonists to block stress-induced potentiation of cocaine place preference (McLaughlin. Marton-Popovici et al. 2003) and to block footshock-induced reinstatement of cocaine self-administration behavior (Beardsley, Howard et al. 2005, Redila and Chavkin 2008). KOP receptor antagonists have also been shown, in rats, to selectively attenuate ethanol-dependent self-administration while leaving nondependent ethanol self-administration intact (Walker and Koob 2007), consistent with earlier findings of a decrease in alcohol self-administration in KOP receptor knockout mice (Kovacs. Szakall et al. 20051).

Naltrexone, predominantly a MOP receptor antagonist, has been shown to be effective over both the short and medium term in preventing relapse to alcohol use, particularly when combined with psychosocial treatment (Rosner. Hackl-Herrwerth et al. 2010). Interestingly, the positive effect in preventing relapse to alcohol is maintained in individuals with dual cocaine/alcohol dependence or abuse (Hersh. Van Kirk et al. 1998), supporting a role for MOP receptor antagonism in reducing alcohol intake in the polydrug using community.

In medicinal chemistry, it is desirable to develop ligands with ever more finely-tuned activity for particular targets so as to increase efficacy and decrease the possibility of side effects. Accordingly, the present invention provides compounds having a mixed affinity profile at opioid and NOP receptors and having: (i) MOP partial agonist/NOP receptor partial agonist and KOP antagonist activity or (ii) MOP and KOP antagonist activity and NOP partial agonist activity.

Compounds exhibiting MOP and NOP receptor agonist activities in combination may potentially be analgesic with low abuse potential and less tolerance development than other conventionally used opioids. Compounds of this type may also be of use in the treatment of opiate abuse. Examples from the current invention include 11, 16 and 17.

Compounds exhibiting MOP/KOP receptor antagonist activity plus NOP receptor partial agonist activity may potentially be useful for the prevention of relapse to drug taking in recovering addicts and in treating depression and anxiety type disorders. Compounds from the current invention include 12, 13 and 14.

Furthermore, in order to understand further the role of mixed ligands at NOP and opioid receptors there is a need to provide a variety of new scaffolds able to provide insights into receptor-ligand binding pockets, their underlying mechanism and pharmacological response. The present invention addresses this need.

The present invention provides active compounds for use in a method of treatment of the human or animal body. Such a method may comprise administering to such a subject a therapeutically-effective amount of an active compound, preferably in the form of a pharmaceutical composition.

The term "treatment", as used herein in the context of treating a condition, pertains generally to treatment and therapy, whether of a human or an animal (e.g. in veterinary applications), in which some desired therapeutic effect is achieved, for example, the inhibition of the progress of the condition, and includes a reduction in the rate of progress, a halt in the rate of progress, amelioration of the condition, and cure of the condition. Treatment as a preventative measure, i.e. prophylaxis, is also included.

The term "therapeutically-effective amount" as used herein pertains to that amount of an active compound, or a material, composition or dosage form comprising an active compound, which is effective for producing some desired therapeutic effect, commensurate with a reasonable benefit/risk ratio.

The compounds of the invention may be used in the treatment of pain, hyperalgesia, addiction, substance abuse disorders, stress, depression, anorexia, anxiety, depression cough, asthma, hypertension, gastrointestinal motility disorder, water retention, a cognitive disorder or a locomotor disorder. Compounds of the invention may also be useful in enhancing cognitive function. Compounds of the invention may be of use in the treatment of subjects having a history of substance abuse, or known to be at risk of developing a substance abuse problem. Such a substance abuse problem may be dependence or an addiction.

In some embodiments, the substance that is abused is a narcotic, for example, heroin or morphine. The substance that is abused may be cocaine or another stimulant, or may be alcohol. Compounds of the invention may also be of use in the prevention of relapse in recovering abusers of these substances. It will be appreciated that substance abuse may relate to abuse of one, or more than one, of these substances.

It should be noted that in all of the above aspects of the present invention, the compound represented by formula 2 may be administered with an additional therapeutic agent, either by being co-formulated with the additional therapeutic agent or by being provided in the form of a kit containing each agent separately formulated for sequential or simultaneous administration. In a preferred embodiment, the additional therapeutic agent is an opioid, for example, morphine. Co- or sequential administration of a compound of the invention may help to ameliorate the negative side effects associated with the additional therapeutic agent.

Administration

The active compound or pharmaceutical composition comprising the active compound may be administered to a subject by any convenient route of administration, whether systemically/peripherally or at the site of desired action, including but not limited to, oral (e.g. by ingestion); topical (including e.g. transdermal, intranasal, ocular, buccal, and sublingual); pulmonary (e.g. by inhalation or insufflation therapy using, e.g. an aerosol, e.g. through mouth or nose); rectal; vaginal; parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot, for example, subcutaneously or intramuscularly.

The subject may be a eukaryote, an animal, a vertebrate animal, a mammal, a rodent (e.g. a guinea pig, a hamster, a rat, a mouse), murine (e.g. a mouse), canine (e.g. a dog), feline (e.g. a cat), equine (e.g. a horse), a primate, simian (e.g. a monkey or ape), a monkey (e.g. marmoset, baboon), an ape (e.g. gorilla, chimpanzee, orang-utan, gibbon), or a human. Preferably, the subject is a human.

Formulations

While it is possible for the active compound to be administered alone, it is preferable to present it as a pharmaceutical composition (e.g. formulation) comprising at least one active compound, as defined above, together with one or more pharmaceutically acceptable carriers, adjuvants, excipients, diluents, fillers, buffers, stabilisers, preservatives, lubricants, or other materials well known to those skilled in the art and optionally other therapeutic or prophylactic agents.

Thus, the present invention further provides pharmaceutical compositions, as defined above, and methods of making a pharmaceutical composition comprising admixing at least one active compound, as defined above, together with one or more pharmaceutically acceptable carriers, excipients, buffers, adjuvants, stabilisers, or other materials, as described herein.

The term "pharmaceutically acceptable" as used herein pertains to compounds, materials, compositions, and/or dosage forms which are, within the scope of sound medical judgement, suitable for use in contact with the tissues of a subject (e.g. human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation.

Suitable carriers, excipients, etc. can be found in standard pharmaceutical texts, for example, 'Remington's Pharmaceutical Sciences', 18th edition, Mack Publishing Company, Easton, Pa., 1990.

The formulations may conveniently be presented in unit dosage form and may be prepared by any methods well known in the art of pharmacy. Such methods include the step of bringing into association the active compound with the carrier which constitutes one or more accessory ingredients. In general, the formulations are prepared by uniformly and intimately bringing into association the active compound with liquid carriers or finely divided solid carriers or both, and then if necessary shaping the product.

Formulations may be in the form of liquids, solutions, suspensions, emulsions, elixirs, syrups, tablets, losenges, granules, powders, capsules, cachets, pills, ampoules, suppositories, pessaries, ointments, gels, pastes, creams, sprays, mists, foams, lotions, oils, boluses, electuaries, or aerosols.

Formulations suitable for oral administration (e.g. by ingestion) may be presented as discrete units such as capsules, cachets or tablets, each containing a predetermined amount of the active compound; as a powder or granules; as a solution or suspension in an aqueous or non-aqueous liquid; or as an oil-in-water liquid emulsion or a water-in-oil liquid emulsion; as a bolus; as an electuary; or as a paste.

A tablet may be made by conventional means, e.g., compression or moulding, optionally with one or more accessory ingredients. Compressed tablets may be prepared by compressing in a suitable machine the active compound in a free-flowing form such as a powder or granules, optionally mixed with one or more binders (e.g. povidone, gelatin, acacia, sorbitol, tragacanth, hydroxypropylmethyl cellulose); fillers or diluents (e.g. lactose, microcrystalline cellulose, calcium hydrogen phosphate); lubricants (e.g. magnesium stearate, talc, silica); disintegrants (e.g. sodium starch glycolate, cross-linked povidone, cross-linked sodium carboxymethyl cellulose); surface-active or dispersing or wetting agents (e.g. sodium lauryl sulfate); and preservatives (e.g. methyl p-hydroxybenzoate, propyl p-hydroxybenzoate, sorbic acid). Moulded tablets may be made by moulding in a suitable machine a mixture of the powdered compound moistened with an inert liquid diluent. The tablets may optionally be coated or scored and may be formulated so as to provide slow or controlled release of the active compound therein using, for example, hydroxypropylmethyl cellulose in varying proportions to provide the desired release profile. Tablets may optionally be provided with an enteric coating, to provide release in parts of the gut other than the stomach.

Formulations suitable for topical administration (e.g. transdermal, intranasal, ocular, buccal, and sublingual) may be formulated as an ointment, cream, suspension, lotion, powder, solution, past, gel, spray, aerosol, or oil. Alternatively, a formulation may comprise a patch or a dressing such as a bandage or adhesive plaster impregnated with active compounds and optionally one or more excipients or diluents.

Formulations suitable for topical administration in the mouth include losenges comprising the active compound in a flavoured basis, usually sucrose and acacia or tragacanth; pastilles comprising the active compound in an inert basis such as gelatin and glycerin, or sucrose and acacia; and mouthwashes comprising the active compound in a suitable liquid carrier.

Formulations suitable for topical administration to the eye also include eye drops wherein the active compound is dissolved or suspended in a suitable carrier, especially an aqueous solvent for the active compound.

Formulations suitable for nasal administration, wherein the carrier is a solid, include a coarse powder having a particle size, for example, in the range of about 20 to about 500 microns which is administered in the manner in which snuff is taken, i.e. by rapid inhalation through the nasal passage from a container of the powder held close up to the nose. Suitable formulations wherein the carrier is a liquid for administration as, for example, nasal spray, nasal drops, or by aerosol administration by nebuliser, include aqueous or oily solutions of the active compound.

Formulations suitable for administration by inhalation include those presented as an aerosol spray from a pressurised pack, with the use of a suitable propellant, such as dichlorodifluoromethane, trichlorofluoromethane, dichlorotetrafluoroethane, carbon dioxide, or other suitable gases.

Formulations suitable for topical administration via the skin include ointments, creams, and emulsions. When formulated in an ointment, the active compound may optionally be employed with either a paraffinic or a water-miscible ointment base. Alternatively, the active compounds may be formulated in a cream with an oil-in-water cream base. If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the active compound through the skin. Examples of such dermal penetration enhancers include dimethylsulfoxide and related analogues.

When formulated as a topical emulsion, the oily phase may optionally comprise merely an emulsifier (otherwise known as an emulgent), or it may comprises a mixture of at least one emulsifier with a fat or an oil or with both a fat and an oil. Preferably, a hydrophilic emulsifier is included together with a lipophilic emulsifier which acts as a stabiliser. It is also preferred to include both an oil and a fat. Together, the emulsifier(s) with or without stabiliser(s) make up the so-called emulsifying wax, and the wax together with the oil and/or fat make up the so-called emulsifying ointment base which forms the oily dispersed phase of the cream formulations.

Suitable emulgents and emulsion stabilisers include Tween 60, Span 80, cetostearyl alcohol, myristyl alcohol, glyceryl monostearate and sodium lauryl sulphate. The choice of suitable oils or fats for the formulation is based on achieving the desired cosmetic properties, since the solubility of the active compound in most oils likely to be used in pharmaceutical emulsion formulations may be very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required.

Alternatively, high melting point lipids such as white soft paraffin and/or liquid paraffin or other mineral oils can be used.

Formulations suitable for parenteral administration (e.g. by injection, including cutaneous, subcutaneous, intramuscular, intravenous and intradermal), include aqueous and non-aqueous isotonic, pyrogen-free, sterile injection solutions which may contain anti-oxidants, buffers, preservatives, stabilisers, bacteriostats, and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. Examples of suitable isotonic vehicles for use in such formulations include Sodium Chloride Injection, Ringer's Solution, or Lactated Ringer's Injection. Typically, the concentration of the active compound in the solution is from about 1 ng/ml to about 10 µg/ml, for example from about 10 ng/ml to about 1 µg/ml. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets. Formulations may be in the form of liposomes or other microparticulate systems which are designed to target the active compound to blood components or one or more organs.

Dosage

It will be appreciated that appropriate dosages of the active compounds, and compositions comprising the active compounds, can vary from patient to patient. Determining the optimal dosage will generally involve the balancing of the level of therapeutic benefit against any risk or deleterious side effects of the treatments of the present invention. The selected dosage level will depend on a variety of factors including, but not limited to, the activity of the particular compound, the route of administration, the time of administration, the rate of excretion of the compound, the duration of the treatment, other drugs, compounds, and/or materials used in combination, and the age, sex, weight, condition, general health, and prior medical history of the patient. The amount of compound and route of administration will ultimately be at the discretion of the physician, although generally the dosage will be to achieve local concentrations at the site of action which achieve the desired effect without causing substantial harmful or deleterious side-effects.

Administration in vivo can be effected in one dose, continuously or intermittently (e.g. in divided doses at appropriate intervals) throughout the course of treatment. Methods of determining the most effective means and dosage of administration are well known to those of skill in the art and will vary with the formulation used for therapy, the purpose of the therapy, the target cell being treated, and the subject being treated. Single or multiple administrations can be carried out with the dose level and pattern being selected by the treating physician.

In general, a suitable dose of the active compound is in the range of about 100 µg to about 250 mg per kilogram body weight of the subject per day. Where the active compound is a salt, an ester, prodrug, or the like, the amount administered is calculated on the basis of the parent compound and so the actual weight to be used is increased proportionately.

Synthesis

Synthetic strategy: The compounds of the invention may be synthesised using methodology known to the skilled person. Suitable methods include, but are not limited to, those discussed herein. Suitable modifications and developments of the methods described in this application will be known to the skilled person. In general, the ester derivatives described herein are preferably prepared from their parent structure (naltrexone esters from naltrexone, nalmefene esters from nalmefene, desoxonaltrexone esters from desoxonaltrexone, and naltrexol esters from naltrexol) by first protecting any hydroxyl group(s) in the molecule other than the C14-hydroxyl, then esterifying at the C14-hydroxyl and then deprotecting the other hydroxyls. Nalmefene, 6-desoxonaltrexone and the naltrexols (α and β) can each be prepared from naltrexone by standard methods. The ether derivatives described herein are prepared by a similar route but the phenolic hydroxyl group at C3 in each of the parent structures is typically protected as the methyl ether. Thus naltrexone methyl ether allows access to the 3-O-methyl ethers of nalmefene, 6-desoxonaltrexone and α- and β-naltrexol and hence to their C14-O ethers. Variations in N-substituent can be readily achieved by utilizing the known chemistry of oxycodone. This can be N-dealkylated to groups may be envisaged. To facilitate a clean esterification reaction with naltrexone, the C6-carbonyl may be, but is not necessarily, protected, for example, as a cyclic ketal or similar. Esterification at C14 may then be accomplished using the appropriate acid anhydride or acyl chloride. Suitable acid anhydrides may be prepared from the appropriate carboxylic acid and triphosgene. The protecting group(s) may then be removed using appropriate methods known in the art.

In the following representative synthesis (Scheme 1), the 3-hydroxyl group of naltrexone and nalmefene (i) is selectively protected using tert-butyldimethylsilyl chloride and imidazole, followed by C14 esterification with the appropriate acid anhydride. Deprotection using TBAF then furnishes the desired C14-ester.

Scheme 1: Reagents and Conditions: a) TBDSMCl, Imidazole, DCM, RT; b) (Q-(CH$_2$)$_n$-CO)$_2$O, PhMe, 125° C.; c) TBAF.

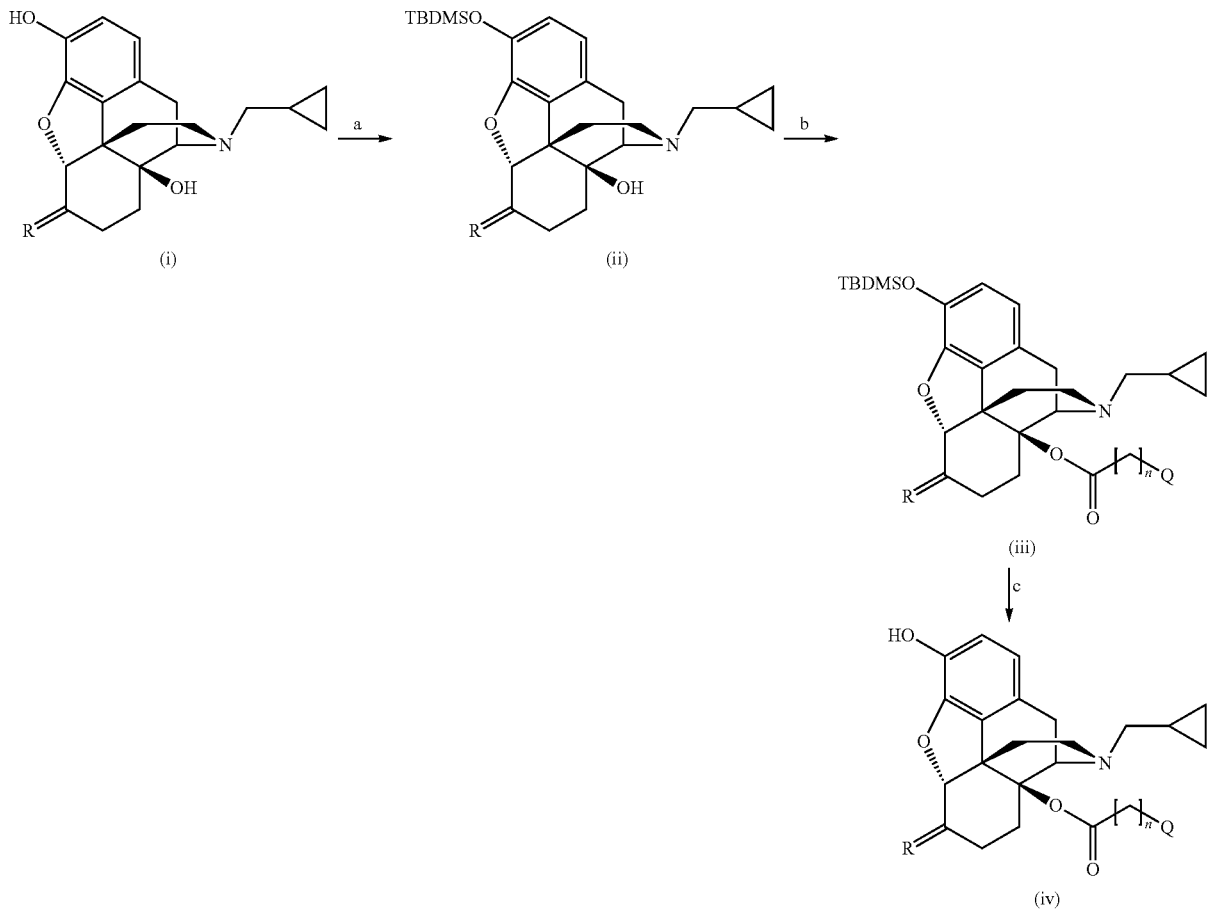

R = O, naltrexone
R = CH$_2$, nalmefene noroxycodone and then alkylated to give the desired N-substituent. The C14-O-ethers are then made from this material while 3-O-demethylation to the N-alkylated noroxymorphone allows access to the corresponding esters.

The synthesis of esters of naltrexone and nalmefene may begin with naltrexone or nalmefene (i). To enable selective esterification of the 14-hydroxy group, the 3-hydroxy group of (i) may be protected using methods and reagents known in the art, for example, using a silyl protecting group such as a tert-butyldimethylsilyl group. Other suitable protecting C14-O esters of the naltrexols (α and β) may be prepared from the appropriate naltrexol by first protecting both the 3- and 6-hydroxy groups, for example as their TBDMS ethers. The C14-OH can then be esterified using an appropriate acylating agent, for example an anhydride, before deprotection of both the 3- and 6-protecting groups. A representative synthesis is shown in Scheme 2. Esters of the naltrexols may also be prepared by reduction of the corresponding naltrexone esters (Scheme 2).

Scheme 2: Reagents and Conditions: a) TBDSMCl, Imidazole, DCM, RT; b) (Q-(CH$_2$)$_n$-CO)$_2$O, PhMe, 125° C; c) TBAF.

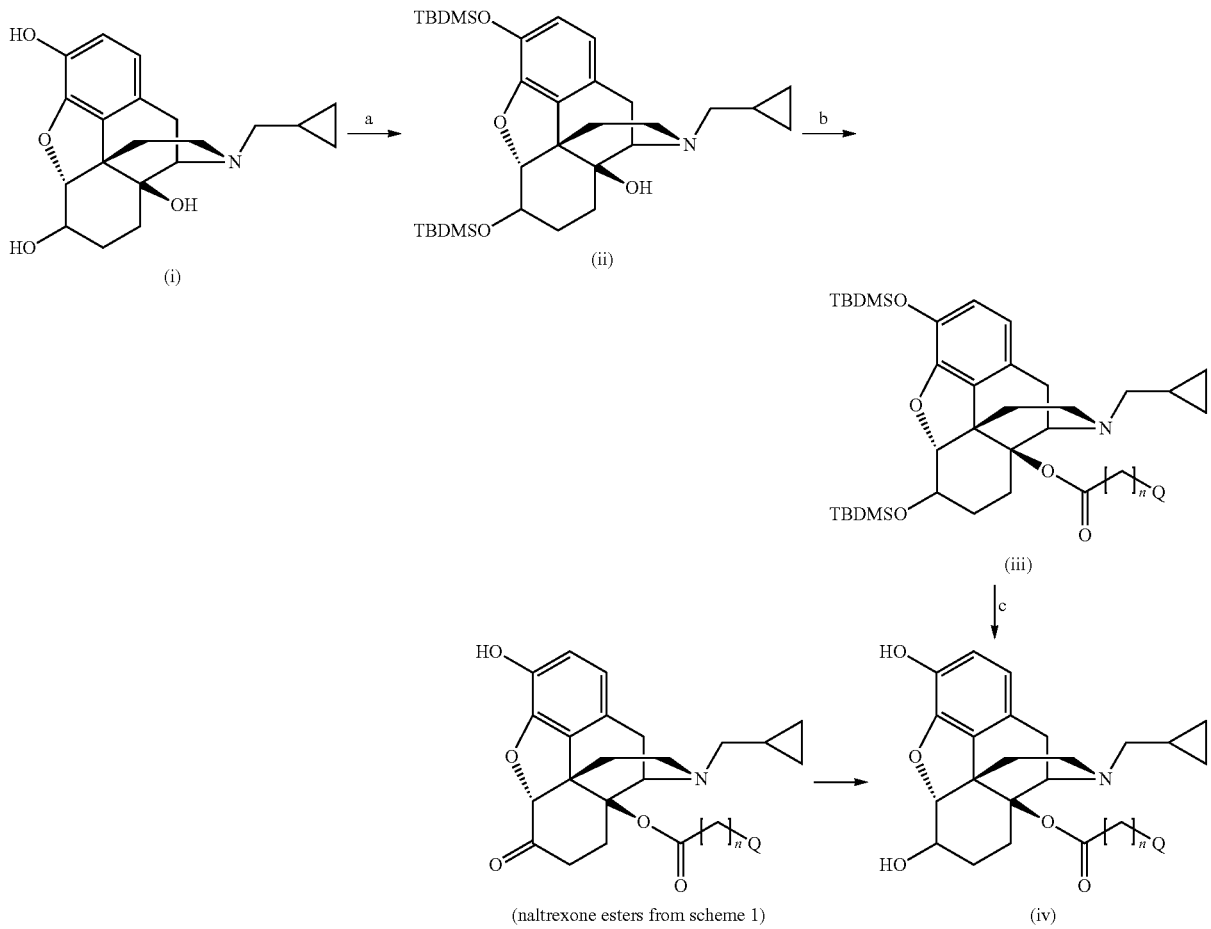

Similar routes may be employed to synthesise ethers of nalmefene and naltrexol. Reactions for the formation of ethers are known and may include displacement of a leaving group, for example, a chloride, bromide, iodide, mesylate or tosylate on a suitable substrate, or by a Mitsunobu reaction.

In the following representative synthesis of nalmefene 14-O phenylpropyl ether the 3-hydroxyl group is protected as the methyl ether, the C14-hydroxy is then derivatised using cinnamyl bromide before hydrogenation to the phenylpropyl ether and finally 3-O-demethylation using boron tribromide (Scheme 3). Direct alkylation of (ii) in Scheme 3 with Q-[CH$_2$]$_n$—CH$_2$Br in the presence of a base such as NaH may also be used.

Scheme 3: Reagents and Conditions: a) MeI, K$_2$CO$_3$, acetone; b) Cinnamyl bromide, NaH, THF, reflux; c) H$_2$, Pd/C; d) BBr$_3$, CH$_2$Cl$_2$; e) Wittig salt, n-BuLi, THF.

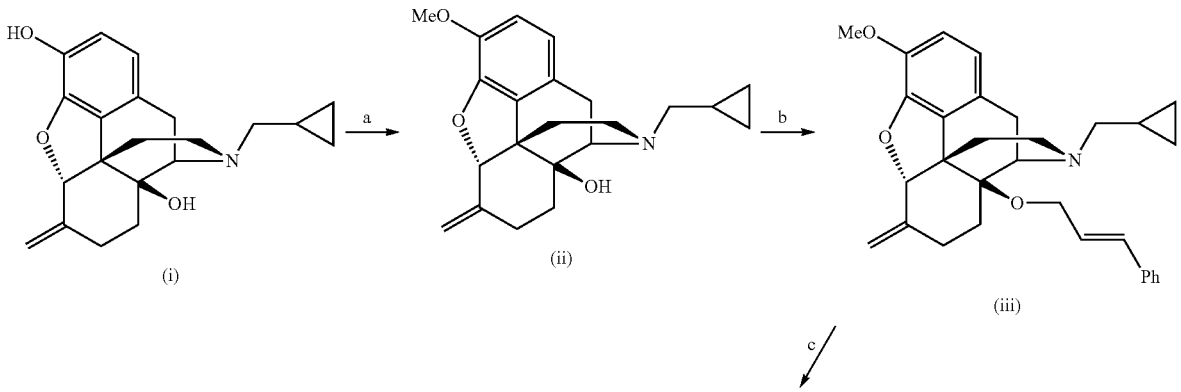

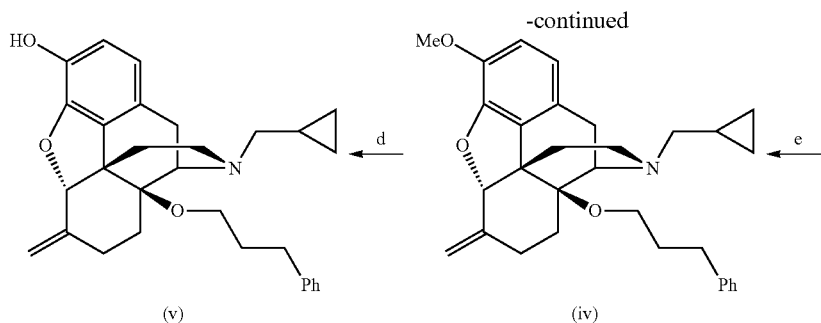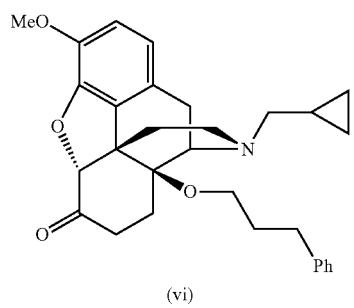

Nalmefene analogues may also be obtained from the corresponding naltrexone analogues by use of a Wittig reaction using, for example, a methyltriphenylphosphonium ylid generated from methyltriphenylphosphonium bromide and a suitable base, for example, potassium tert-butoxide or sodium or potassium methoxide or sodium hydride.

Ethers of naltrexol can be prepared from the corresponding naltrexone ester using similar methods. In the following representative synthesis of 6β-naltrexol 14-O phenylpropyl ether the C6-keto group of naltrexone is protected as the ketal and the C3-hydroxyl group is protected as the methyl ether, the C14-hydroxy is then derivatised using cinnamyl bromide before hydrogenation to the phenylpropyl ether (Scheme 4). Deprotection at C6 was achieved with aq. HCl and finally 3-O-demethylation using boron tribromide. The 6-keto group is then reduced to the corresponding alcohol. Reduction using a reducing agent such as $NaBH_4$ gives access to the 6α-epimer while reduction with formamidinesulfinic acid/NaOH gives the 6β-epimer.

Scheme 4: : Reagents and Conditions: a) Glycol, $CH_3SO_3H$, 90° C., 20h; b)MeI; c)Cinnamyl bromide, NaH, THF, reflux; d) $H_2$, Pd/C; e) MeOH:HCl (6N) 1:1, reflux; f) $BBr_3$, $CH_2Cl_2$; g) formamidinesulfonic acid/NaOH

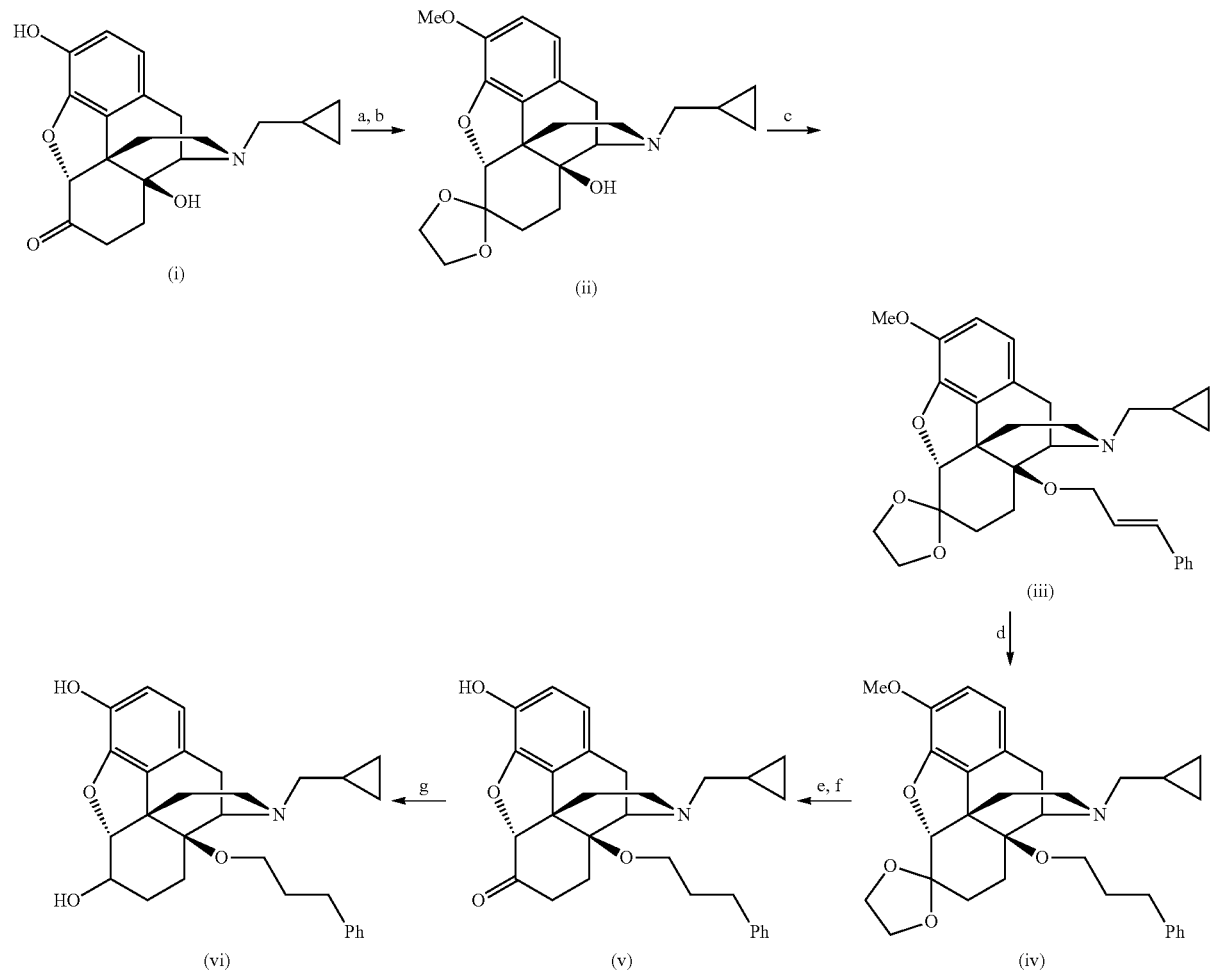

Ethers and esters of 6-deoxonaltrexone can be prepared from 6-desoxonaltrexone by first protecting the C3-hydroxyl as described for the previous examples, before then acylating or alkylating the C14-hydroxyl. The following representative syntheses illustrate this for the formation of the phenylpropyl ether and phenylpropanoyl ester (Scheme 5).

Scheme 5: Reagents and Conditions: a) TBDSMCl, Imidazole, DCM, RT; b) (Ph(CH$_2$)$_2$CO)$_2$O, c) TBAF; d) MeI e) Cinnamyl bromide, NaH, THF, reflux; f) H$_2$, Pd/C; g) BBr$_3$, CH$_2$Cl$_2$.

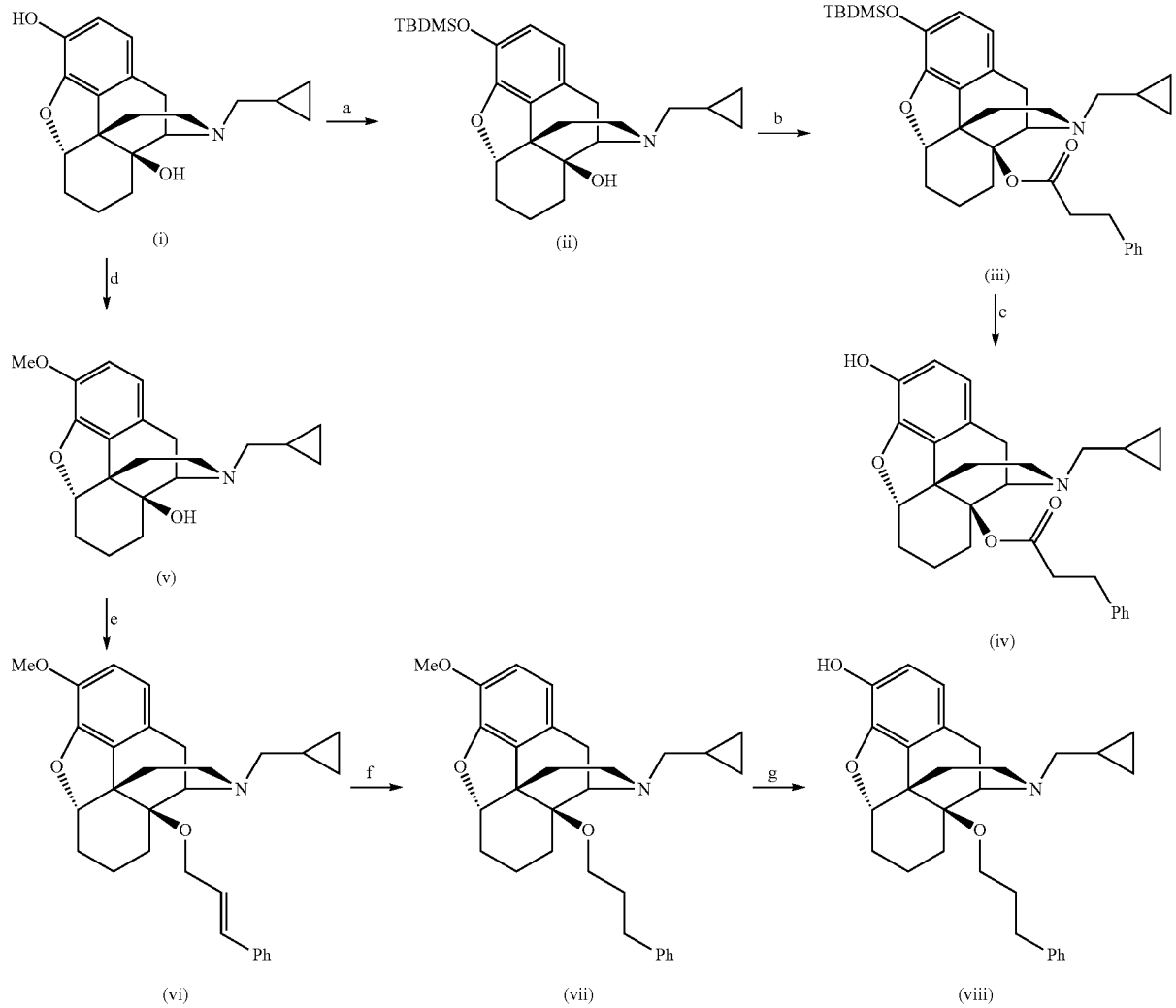

Preparation of 6-Ethylene Ketal

The appropriate 6-keto compound (10 mmol) was dissolved in 20 ml of ethylene glycol under an atmosphere of N$_2$. To it methane sulphonic acid (0.94 mL, 14.5 mmol) was added dropwise under constant stirring and the reaction heated to 90° C. for 20 h. After completion the reaction mixture was cooled to room temperature and diluted with 100 mL of water. The reaction mixture was neutralized with ammonium hydroxide, extracted with dichloromethane (3×50 mL). The organic layer was washed with water (2×50 mL), brine (50 mL) dried over magnesium sulphate and concentrated under reduced pressure to obtain the title product which was re-crystallized in methanol (4.95 g).

Preparation of 3-O-[(1,1-dimethylethyl)dimethylsilyl]ether

To a solution of the phenolic compound (10 mmol) in dichloromethane (40 mL), methylimidazole (1.77 g, 26 mmol) was added and reaction mixture was stirred for 5 min under N$_2$. Thereafter tert-butyldimethylsilyl chloride (1.88 g, 12.5 mmol) was added in a small lots and reaction mixture was stirred at room temperature for 5 h. Upon completion the reaction mixture was diluted with 100 mL of water. The aqueous layer extracted with dichloromethane (2×50 mL), washed with water (2×40 mL), brine (40 mL), dried over magnesium sulphate and vacuum evaporated to obtained the title product which was re-crystallized in methanol (4.85 g).

Preparation of Acyl Anhydrides

To a solution of optionally substituted phenylacetic acid (2 mmol) in anhydrous ethyl acetate (20 mL) at 0° C., triethylamine (0.28 ml, 2 mmol) was added dropwise under an N$_2$ atmosphere. After 5 min of stirring, triphosgene (0.10 g, 0.35 mmol) was added and the reaction mixture was stirred for 3 h at room temperature. After completion of the reaction, the reaction mixture was passed through Celite® and concentrated under vacuum to obtain the anhydrides.

Preparation of 14-O-esters

To a solution of 14-hydroxy compound, (e.g. 3-O-[(1,1-dimethylethyl)dimethylsilyl]naltrexone ethylene ketal) (0.4 mmol) in anhydrous toluene, optionally substituted phenylacetic anhydride (0.8 mmol) and DMAP (0.04 mmol) were added and the reaction mixture was refluxed for 16 h. After completion of reaction, saturated sodium bicarbonate (15 mL) was added and the aqueous layer was extracted with EtOAc (3×10 mL). The organic layer was washed with water (2×20 mL), brine (10 mL) and dried over magnesium sulphate and evaporated in vacuo to obtain crude product which was purified by flash chromatography using methanol:dichloromethane (0.5:99.5).

For the synthesis of 14-O-esters of α- and β-naltrexol both the 3- and 6-OH groups were protected as their TBDMS ether prior to the 14-O-acylation procedure.

Deprotection of TBDMS Ethers and Ethylene Ketal.

The substrate (0.3 g) was dissolved in 6 mL (1:1) solution of methanol:hydrochloric acid (6N) and refluxed for 5 h. The reaction mixture was cooled to 0° C. and neutralized with saturated sodium bicarbonate. The organic layer extracted with ethyl acetate (3×20 ml), washed with water (2×25 mL), brine (25 mL), dried over magnesium sulphate and vacuum evaporated to obtained crude product which was purified by flash chromatography using methanol:dichloromethane:ammonium hydroxide (2:97.5:0.5).

Preparation of 14-O-ethers of Nalmefene

To a stirred solution of methyltriphenylphosphonium bromide (Wittig salt) (194 mg, 0.48 mmol), in dry THF (2 mL) was added dropwise a 1.6 M solution of n-BuLi (300 μl, 0.48 mmol), at −40° C. and immediately the colour became orange. After 30 min the appropriate 14-O-ether of naltrexone-3-OMe ether (e.g. vi, scheme 3: 0.40 mmol) in THF (2 mL), was added dropwise at −40° C. to the above solution and stirred until the orange colour disappeared. The reaction was then stirred at room temperature for 4 h. After completion of the reaction, a saturated solution of NH$_4$Cl (6 mL, was added and products extracted with EtOAc (3×10 mL). The extracts were washed with water and brine, dried over MgSO$_4$ and evaporated to dryness. The resulting cream solid was purified by column chromatography over 12 g Rf silica column using Rf Combi flash machine (30%-50% ethyl acetate in hexane) R$_f$=0.88 (30% EtOAc/Hexane, 0.5% NH$_3$) affording 14-(3'-phenylpropyl)-nalmefene (iv in scheme 3) as white solid (47%).

To a solution of this material (iv in scheme 3) (0.11 mmol), in 1 mL, of CH$_2$Cl$_2$ was added a 1M solution of BBr$_3$ in CH$_2$Cl$_2$ (0.65 mL), over 10 minutes at −15° C. while stirring. After 5 min ice 1 g) and 0.6 mL of concentrated NH$_3$ were added and the resulting mixture was stirred at 0° C. for 30 min. The organic layer was separated and the aqueous layer extracted within CH$_2$Cl$_2$ (3×5 mL), the combined organic layers were washed with brine, dried over Na$_2$SO$_4$ and evaporated to dryness. The resulting material was purified by column chromatography over silica gel. Example 32 (22%).

Preparation of 14-O-ethers of 6β-naltrexol

To the appropriate 14-O-ether of naltrexone (e.g. v, scheme 4: 1.32 mmol), formamidine sulfinic acid (5.29 mmol), 2N aqNaOH (5 mL) were stirred and heated to 65° C. under N$_2$. After 2 hours 3N aqNaOH (0.5 mL) was added. The reaction was kept at this temperature for another 2 h and then cooled. The pH of the reaction solution was adjusted to 10-10.5 using saturated ammonium chloride solution. The product precipitated as a white solid and was separated by filtration. Example 31 was isolated as a white solid (69%).

EXAMPLES

The following examples are provided solely to illustrate the present invention and are not intended to limit the scope of the invention, as described herein.

The following compounds were made:

| Compound No. | Structure |
|---|---|
| 1 | (structure) |
| 2 | (structure) |
| 3 | (structure) |
| 4 | (structure) |

| Compound No. | Structure |
|---|---|
| 5 | 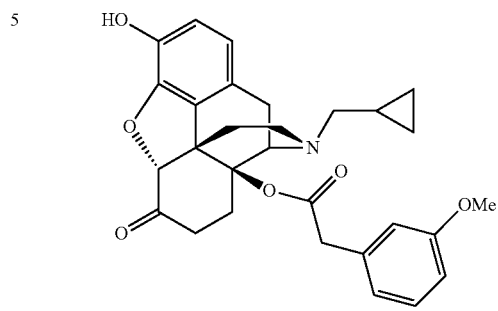 |
| 6 | 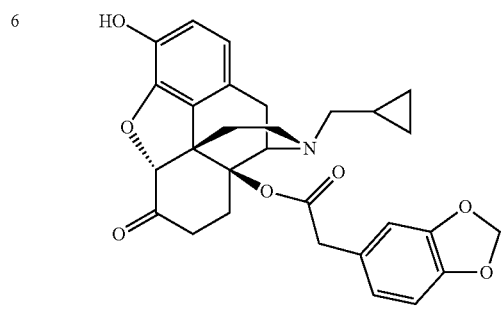 |
| 7 | 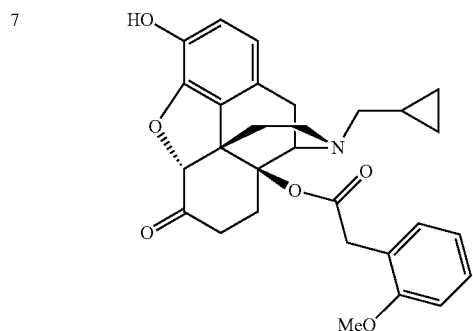 |
| 8 | 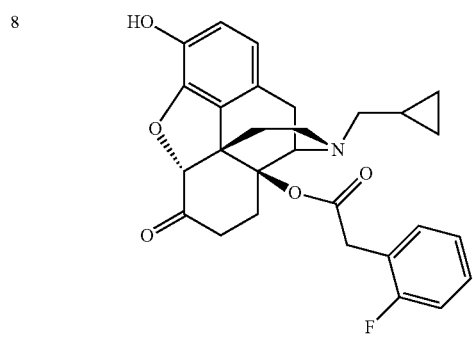 |
| Compound No. | Structure |
|---|---|
| 9 | 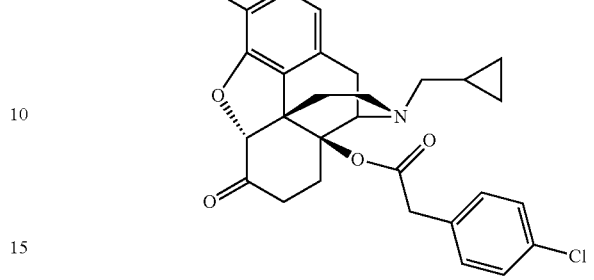 |
| 10 | 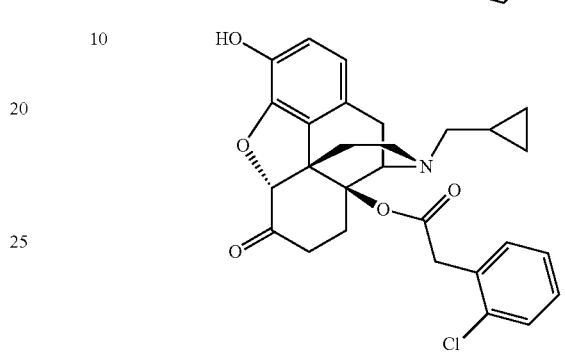 |
| 11 | 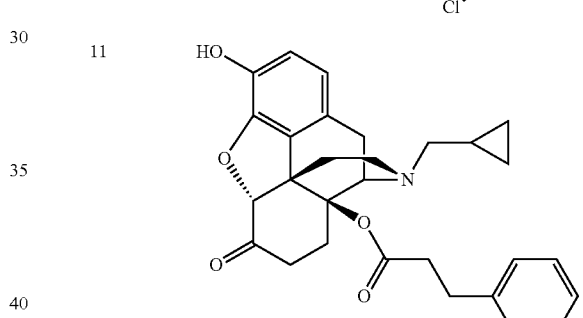 |
| 12 | 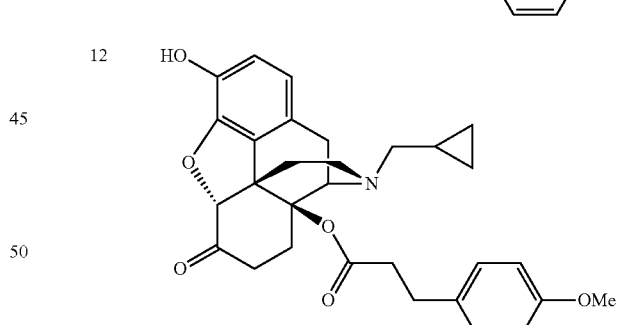 |
| 13 | 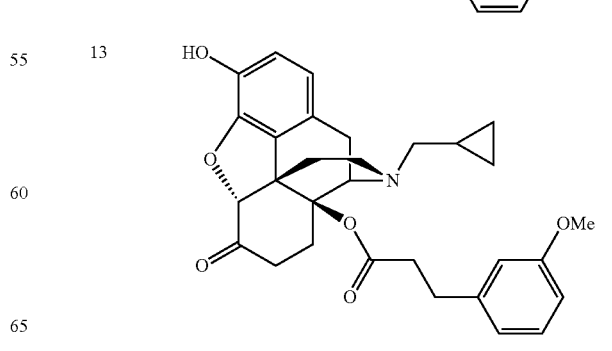 |

| Compound No. | Structure |
|---|---|
| 14 | 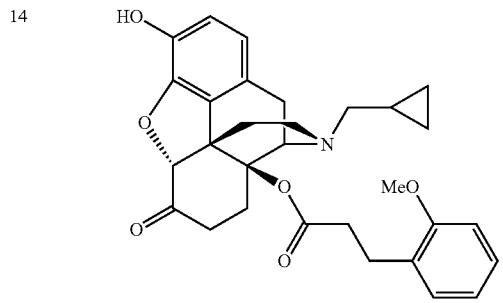 |
| 15 | 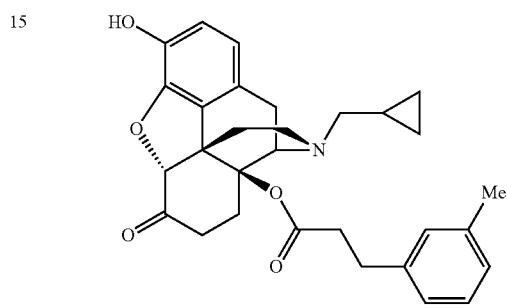 |
| 16 | 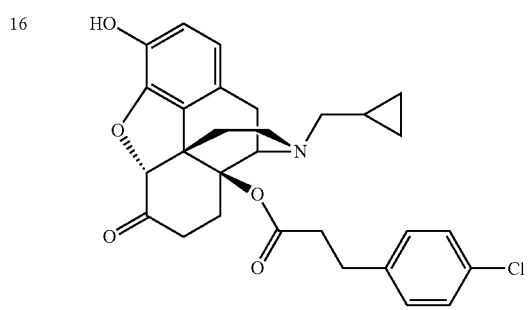 |
| 17 | 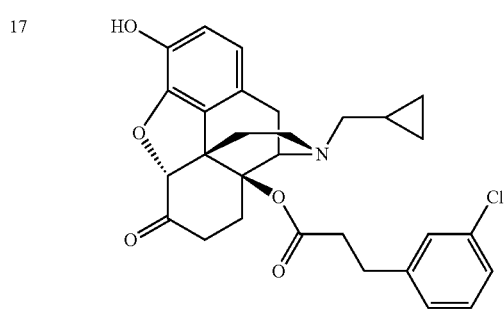 |
| 18 | 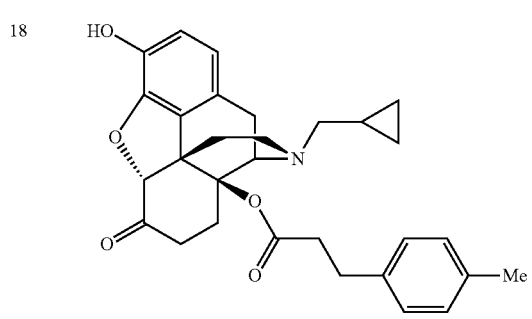 |
| Compound No. | Structure |
|---|---|
| 19 | 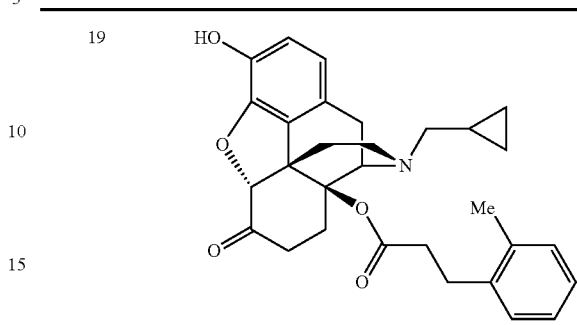 |
| 20 | 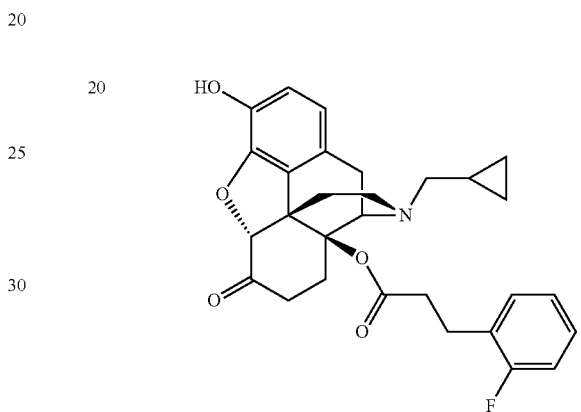 |
| 21 | 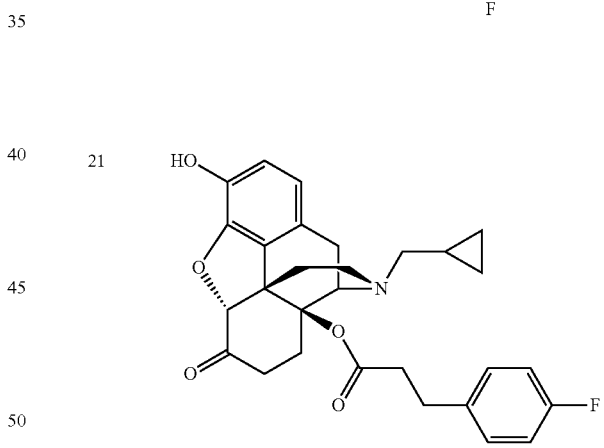 |
| 22 | 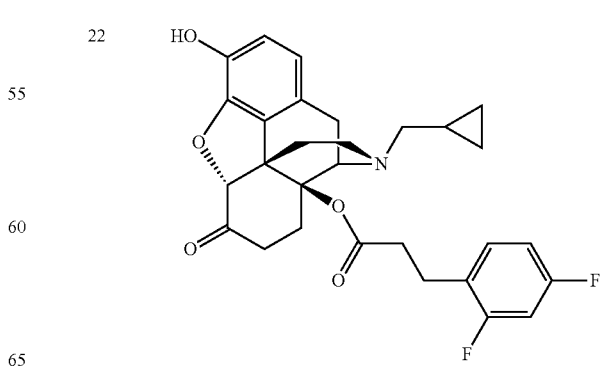 |

| Compound No. | Structure |
|---|---|
| 23 | 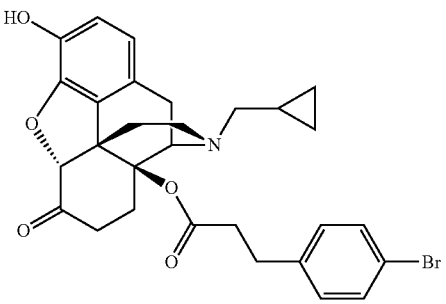 |
| 24 | 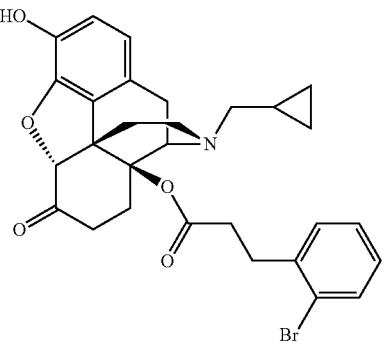 |
| 25 | 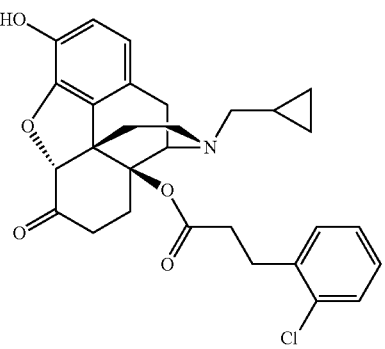 |
| 26 | 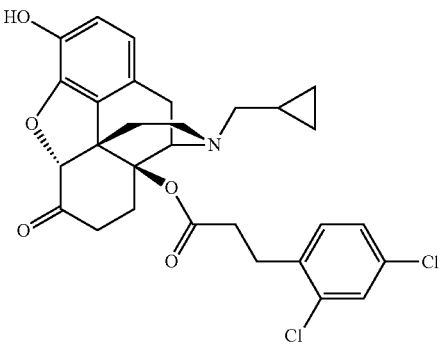 |
| Compound No. | Structure |
|---|---|
| 27 | 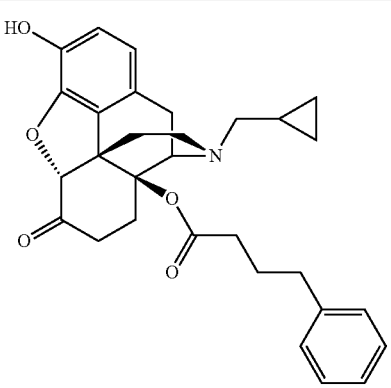 |
| 28 | 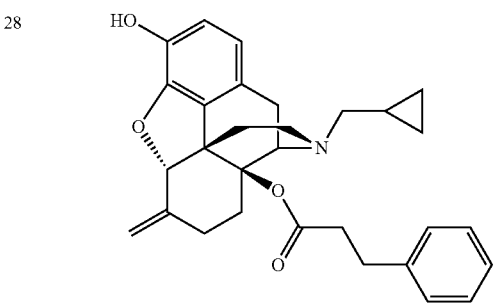 |
| 29 | 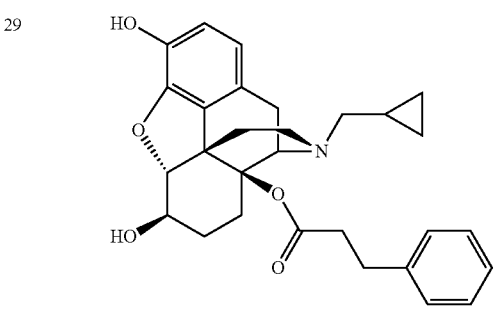 |
| 30 | 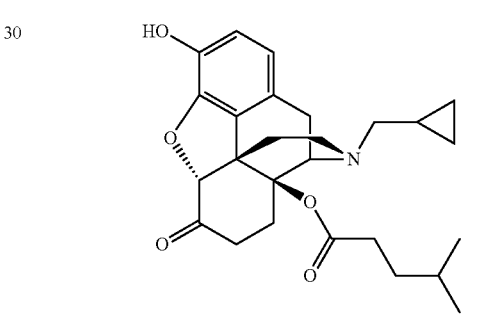 |

| Compound No. | Structure |
|---|---|
| 31 | (structure: 14β-hydroxy morphinan with N-cyclopropylmethyl and O-(3-phenylpropyl) ether) |
| 32 | (structure: methylene-substituted morphinan with N-cyclopropylmethyl and O-(3-phenylpropyl) ether) |

14β-phenylacetyl-17-cyclopropylmethyl-7,8-dihydronoroxmorphinone (1)

White Solid; $^1$H NMR (CDCl$_3$) δ 0.09-0.12 (2H, m), 0.51-0.54 (2H, m), 0.78-0.83 (1H, m), 1.41-1.45 (1H, m), 1.57 (1H, dt, J=3.72 Hz & 14.44 Hz), 2.09-2.21 (2H, m), 2.23-2.52 (4H, m), 2.58-2.67 (2H, m), 2.79-2.82 (1H, m), 3.07 (1H, d, J=18.2 Hz), 3.77 (2H, m), 4.44 (1H, d, J=5.52 Hz), 4.51 (1H, s), 6.59 (1H, d, J=8.0 Hz), 6.72 (1H, d, J=8.0 Hz), 7.24-7.31 (2H, m), 7.36-7.41 (3H, m); $^{13}$C NMR, 400 MHz, (CDCl$_3$) δ 3.81, 9.43, 23.13, 26.86, 29.99, 35.46, 42.91, 43.89, 51.21, 55.64, 59.51, 82.88, 90.16, 117.95, 119.97, 125.18, 127.19, 128.07, 128.56, 129.41, 134.51, 138.72, 143.35, 170.19, 208.18. HRMS, m/z for (C$_{28}$H$_{30}$NO$_5$) [MH]$^+$, calcd—460.2124. found—460.2103. Anal. (C$_{28}$H$_{29}$NO$_5$·HCl·1.75H$_2$O) C, H, N.

14β-(4'-methylphenylacetyl)-17-cyclopropylmethyl-7,8-dihydronoroxymorphinone (2)

White Solid; $^1$H NMR (CDCl$_3$) δ 0.09-0.12 (2H, m), 0.50-0.54 (2H, m), 0.74-0.80 (1H, m), 1.44-1.48 (1H, m), 1.61 (1H, dt, J=3.72 Hz & 14.44 Hz), 2.14-2.22 (2H, m), 2.27-2.51 (8H, m), 2.57-2.61 (1H, m), 2.78-2.82 (1H, m), 3.07 (1H, d, J=18.2 Hz), 3.74-3.76 (2H, m), 4.48 (1H, d, J=5.52 Hz), 4.53 (1H, s), 6.60 (1H, d, J=8.0 Hz), 6.72 (1H, d, J=8.0 Hz), 7.16 (2H, d, J=8.0 Hz), 7.27 (2H, d, J=8.0 Hz); $^{13}$C NMR, 400 MHz, (CDCl$_3$) δ 3.77, 3.83, 9.44, 21.07, 23.15, 26.87, 30.00, 35.48, 42.44, 43.88, 51.23, 55.68, 59.51, 82.76, 90.17, 118.00, 119.98, 125.20, 128.10, 129.06, 129.22, 131.41, 136.79, 138.73, 143.36, 170.46, 208.42. HRMS, m/z for (C$_{29}$H$_{32}$NO$_5$) [MH]$^+$, calcd—474.2280. found—474.2329. Anal. (C$_{29}$H$_{31}$NO$_5$·HCl·H$_2$O) C, H, N.

14β-(2'-methylphenylacetyl)-17-cyclopropylmethyl-7,8-dihydronoroxymorphinone (3)

White Solid; $^1$H NMR (CDCl$_3$) δ 0.09-0.14 (2H, m), 0.51-0.55 (2H, m), 0.78-0.84 (1H, m), 1.32-1.35 (1H, m), 1.51 (1H, dt, J=3.72 Hz & 14.44 Hz), 2.10-2.50 (10H, m), 2.62-2.68 (1H, m), 2.74-2.81 (1H, m), 3.03 (1H, d, J=18.2 Hz), 3.76-3.88 (2H, m), 4.42 (1H, s), 4.51 (1H, d, J=5.52 Hz), 5.90 (1H, bd), 6.59 (1H, d, J=8.0 Hz), 6.72 (1H, d, J=8.0 Hz), 7.20-7.23 (3H, m), 7.29-7.33 (1H, m); $^{13}$C NMR, 400 MHz, (CDCl$_3$) δ 3.80, 3.86, 9.37, 19.62, 23.07, 26.85, 29.86, 35.40, 40.54, 43.94, 51.17, 55.65, 59.59, 82.81, 90.15, 117.99, 119.99, 125.18, 126.15, 127.60, 128.07, 130.24, 130.33, 133.24, 136.66, 138.68, 143.33, 170.03, 208.26. HRMS, m/z for (C$_{29}$H$_{32}$NO$_5$) [MH]$^+$, calcd—474.2280. found—474.2258. Anal. (C$_{29}$H$_{31}$NO$_5$·HCl·0.5H$_2$O) C, H, N.

14β-(3'-methylphenylacetyl-17-cyclopropylmethyl-7,8-dihydronoroxymorphinone (4)

White Solid; $^1$H NMR (CDCl$_3$) δ 0.09-0.12 (2H, m), 0.50-0.54 (2H, m), 0.70-0.75 (1H, m), 1.45-1.49 (1H, dd, J=4.00 Hz & 12.1 Hz), 1.59-1.66 (1H, dt, J=3.72 Hz & 14.44 Hz), 2.14-2.31 (2H, m), 2.32-2.40 (8H, m), 2.67 (1H, dd, J=4.0 Hz & 12.1 Hz), 2.76-2.81 (1H, m), 3.07 (1H, d, J=18.4 Hz), 3.69 (2H, dd, J=8.0 Hz & 18.4 Hz), 4.49 (1H, d, J=4.0 Hz), 4.53 (1H, s), 5.75 (1H, bd), 6.60 (1H, d, J=8.0 Hz), 6.73 (1H, d, J=8.0 Hz), 7.11 (1H, d, J=6.1 Hz), 7.17 (3H, d, J=8.1 Hz); $^{13}$C NMR, 400 MHz, (CDCl$_3$) δ 3.79, 3.81, 9.42, 21.35, 23.13, 26.83, 29.98, 35.45, 42.82, 43.91, 51.21, 55.63, 59.51, 82.80, 90.19, 117.89, 119.97, 125.27, 126.44, 127.88, 128.12, 128.45, 130.16, 134.39, 138.17, 138.63, 143.33, 170.32, 208.19. HRMS, m/z for (C$_{29}$H$_{32}$NO$_5$) [MH]$^+$, calcd—474.2280. found—474.2288. Anal. (C$_{29}$H$_{31}$NO$_5$·HCl·1.5H$_2$O) C, H, N.

14β-(3'-methoxyphenylacetyl)-17-cyclopropylmethyl-7,8-dihydronoroxymorphinone (5)

White Solid; $^1$H NMR (CDCl$_3$) δ 0.09-0.14 (2H, m), 0.50-0.0.54 (2H, m), 0.69-0.74 (1H, m), 1.45-1.49 (1H, dd, J=4.00 Hz & 12.1 Hz), 1.59-1.66 (1H, dt, J=3.72 Hz & 14.44 Hz), 2.14-2.31 (2H, m), 2.31-2.41 (5H, m), 2.67 (1H, dd, J=4.0 Hz & 12.1 Hz), 2.76-2.81 (1H, m), 3.07 (1H, d, J=18.4 Hz), 3.71 (2H, dd, J=8.0 Hz & 18.4 Hz), 3.83 (3H, s), 4.49 (1H, d, J=4.0 Hz), 4.54 (1H, s), 5.79 (1H, bd), 6.60 (1H, d, J=8.0 Hz), 6.73 (1H, d, J=8.0 Hz), 6.83 (1H, dd, J=4.0 Hz & 8.1 Hz), 6.95-6.99 (2H, m), 7.28-7.30 (1H, m); $^{13}$C NMR, 400 MHz, (CDCl$_3$) δ 3.78, 3.83, 9.44, 23.13, 26.87, 30.02, 35.47, 42.90, 43.90, 51.24, 55.25, 55.61, 59.48, 82.89, 90.20, 112.24, 115.59, 117.97, 120.00, 121.78, 125.24, 128.08, 129.54, 135.90, 138.67, 143.33, 159.83, 170.06, 208.29. HRMS, m/z for (C$_{29}$H$_{32}$NO$_6$) [MH]$^+$, calcd—490.2230. found—490.2278. Anal. (C$_{29}$H$_{31}$NO$_6$·HCl·0.25H$_2$O) C, H, N.

14β-(3',4'-dioxymethylenephenylacetyl)-7-cyclopropylmethyl-7,8-dihydronoroxymorphinone (6)

White Solid; $^1$H NMR (CDCl$_3$) δ 0.09-0.14 (2H, m), 0.51-0.54 (2H, m), 0.89-0.95 (1H, m), 1.46-1.51 (1H, m), 1.57 (1H, dt, J=3.76 Hz & 14.44 Hz), 2.11-2.31 (3H, m), 2.36-2.46 (4H, m), 2.65-2.72 (1H, m), 2.76-2.82 (1H, m), 3.08 (1H, d, J=18.2 Hz), 3.68-3.72 (2H, m), 4.49 (1H, d, J=5.52 Hz), 4.58 (1H, s), 5.50 (1H, bd), 5.97 (2H, s), 6.61 (1H, d, J=8.0 Hz), 6.73 (1H, d, J=8.0 Hz), 6.79-6.82 (2H, m), 6.92 (1H, s); $^{13}$C NMR, 400 MHz, (CDCl$_3$) δ 3.80, 3.85, 9.41, 23.13, 26.86, 30.03, 35.52, 42.41, 43.90, 51.24, 53.40, 55.63, 59.52, 82.92, 90.21, 101.08, 108.27, 109.88, 117.90, 120.01, 122.49, 125.27, 128.05, 138.64, 143.32, 146.72, 147.82, 170.33, 208.13. HRMS, m/z for (C$_{29}$H$_{30}$NO$_7$)

[MH]⁺, calcd—504.2022. found—504.2069. Anal. ($C_{29}H_{29}NO_7 \cdot HCl \cdot 0.5H_2O$) C, H, N.

14β-(2'-methoxyphenylacetyl)-17-cyclopropylmethyl-7,8-dihydronoroxmorphinone (7)

White Solid; ¹H NMR (CDCl₃) δ 0.08-0.11 (2H, m), 0.49-0.52 (2H, m), 0.78-0.84 (1H, m), 1.32-1.35 (1H, m), 1.51 (1H, dt, J=3.72 Hz & 14.44 Hz), 2.10-2.45 (6H, m), 2.55-2.65 (2H, m), 2.74-2.81 (1H, m), 3.03 (1H, d, J=18.2 Hz), 3.76 (2H, m), 3.81 (3H, s), 4.34 (1H, s), 4.43 (1H, d, J=5.52 Hz), 5.61 (1H, bd), 6.55 (1H, d, J=8.0 Hz), 6.68 (1H, d, J=8.0 Hz), 6.89 (1H, d, J=8.0 Hz), 6.93 (1H, m), 7.24-7.28 (2H, m); ¹³C NMR, 400 MHz, (CDCl₃) δ 3.78, 3.99, 9.44, 23.19, 26.87, 29.87, 35.33, 37.36, 43.85, 51.12, 55.32, 55.73, 59.25, 82.33, 90.21, 110.26, 117.92, 119.91, 120.59, 123.55, 125.29, 128.17, 128.65, 131.09, 138.65, 143.35, 157.43, 170.27, 208.79. HRMS, m/z for ($C_{29}H_{32}NO_6$) [MH]⁺, calcd—490.2230. found—490.2228. Anal. ($C_{29}H_{31}NO_6 \cdot HCl \cdot 1.25H_2O$) C, H, N.

14β-(2'-fluorophenylacetyl)-17-cyclopropylmethyl-7,8-dihydronoroxymorphinone (8)

White Solid; ¹H NMR (CDCl₃) δ 0.06-0.09 (2H, m), 0.48-0.0.51 (2H, m), 0.71-0.75 (1H, m), 1.33-1.36 (1H, m), 1.56-1.64 (1H, dt, J=3.72 Hz & 14.44 Hz), 2.04-2.42 (6H, m), 2.46-2.62 (2H, m), 2.76-2.80 (1H, m), 3.07 (1H, d, J=18.4 Hz), 3.72 (2H, m), 4.42 (1H, d, J=4.0 Hz), 4.44 (1H, s), 5.65 (1H, bd), 6.56 (1H, d, J=8.0 Hz), 6.68 (1H, d, J=8.0 Hz), 7.08-7.14 (2H, m), 7.25-7.29 (1H, m) 7.35-7.37 (1H, m); ¹³C NMR, 400 MHz, (CDCl₃) δ 3.72, 3.83, 9.44, 23.16, 26.95, 29.87, 35.43, 36.01, 43.82, 51.20, 55.68, 59.50, 83.09, 90.21, 115.21, 115.43, 117.97, 120.00, 124.15, 125.19, 128.04, 129.17, 129.25, 131.57, 138.68, 143.31, 169.09, 208.22. HRMS, m/z for ($C_{28}H_{29}FNO_5$) [MH]⁺, calcd—478.2030. found—478.2073. Anal. ($C_{28}H_{28}FNO_5 \cdot HCl \cdot 1.5H_2O$) C, H, N.

14β-(4'-chlorophenylacetyl)-17-cyclopropylmethyl-7,8-dihydronoroxymorphinone (9)

White Solid; ¹H NMR (CDCl₃) δ 0.04-0.10 (2H, m), 0.47-0.50 (2H, m), 0.65-0.69 (1H, m), 1.43-1.46 (1H, m), 1.59 (1H, dt, J=3.72 Hz & 14.44 Hz), 2.08-2.16 (1H, m), 2.21-2.34 (4H, m), 2.39-2.48 (2H, m), 2.62-2.65 (1H, m), 2.74-2.81 (1H, m), 3.04 (1H, d, J=18.2 Hz), 3.72-3.74 (2H, m), 4.43 (1H, d, J=5.52 Hz), 4.53 (1H, s), 6.56 (1H, d, J=8.0 Hz), 6.70 (1H, d, J=8.0 Hz), 7.29-7.31 (4H, m); ¹³C NMR, 400 MHz, (CDCl₃) δ 3.78, 3.84, 9.41, 23.14, 25.65, 26.93, 30.02, 35.54, 42.06, 43.89, 51.25, 55.64, 59.54, 83.25, 90.15, 118.02, 120.01, 125.15, 127.99, 128.51, 128.68, 130.78, 130.88, 132.84, 133.16, 138.70, 143.34, 169.77, 208.03. HRMS, m/z for ($C_{28}H_{29}ClNO_5$) [MH]⁺, calcd—494.1734. found—494.1734. Anal. ($C_{28}H_{28}ClNO_5 \cdot HCl \cdot H_2O$) C, H, N.

14β-(2'-chlorophenylacetyl)-17-cyclopropylmethyl-7,8-dihydronoroxymorphinone (10)

White Solid; ¹H NMR (CDCl₃) δ 0.08-0.10 (2H, m), 0.49-0.53 (2H, m), 0.76-0.81 (1H, m), 1.30-1.33 (1H, m), 1.56 (1H, dt, J=3.72 Hz & 14.44 Hz), 2.04-2.09 (2H, m), 2.25-2.32 (2H, m), 2.41-2.46 (2H, m), 2.53-2.59 (2H, m), 2.76-2.81 (1H, m), 3.03 (1H, d, J=18.2 Hz), 3.90 (2H, m), 4.41 (1H, d, J=4.0 Hz), 4.43 (1H, s), 5.48 (1H, bd), 6.55 (1H, d, J=8.0 Hz), 6.68 (1H, d, J=8.0 Hz), 7.24-7.26 (2H, m), 7.40-7.43 (2H, m); ¹³C NMR, 400 MHz, (CDCl₃) δ 3.78, 3.90, 9.54, 23.16, 26.97, 29.85, 35.52, 40.54, 43.82, 51.15, 55.71, 59.56, 83.11, 90.24, 117.84, 119.95, 125.20, 126.95, 128.06, 128.82, 129.52, 131.60, 132.95, 134.53, 138.61, 143.29, 168.89, 208.08. HRMS, m/z for ($C_{28}H_{29}ClNO_5$) [MH]⁺, calcd—494.1734. found—494.1729. Anal. ($C_{28}H_{28}ClNO_5 \cdot HCl \cdot 0.25H_2O$) C, H, N.

14β-Phenylpropanoyl-17-cyclopropylmethyl-7,8-dihydronoroxymorphinone (11)

White solid. R_f 0.32 (at 30% EtOAc/Hexane, 0.5% NH₃), ¹H NMR (400 MHz, CDCl₃) δ 0.06-0.08 (2H, d, J=8.0 Hz), 0.47-0.49 (2H, d, J=8.0 Hz), 0.73 (1H, m), 1.47-1.50 (1H, d, J=9.7 Hz), 1.57-1.61 (1H, t, J=14.5 Hz), 2.11-2.17 (2H, m), 2.24-2.35 (3H, m), 2.42-2.49 (3H, m), 2.67-2.70 (1H, m), 2.74-2.85 (3H, m), 3.01-3.06 (2H, m), 3.03-3.08 (1H, d, J=16.0 Hz), 4.43-4.44 (1H, d, J=5.5 Hz), 4.57 (1H, s), 6.56-6.58 (2H, d, J=8.0 Hz), 6.69-6.71 (2H, d, J=8.0 Hz), 7.18-7.31 (5H, m); ESIMS m/z: 474.240 [M+1]⁺.

14β-(4'-methoxyphenylpropanoyl)-17-cyclopropylmethyl-7,8-dihydronoroxymorphinone (12)

White Solid; ¹H NMR (CDCl₃) δ 0.06-0.08 (2H, m), 0.46-0.50 (2H, m), 0.68-0.72 (1H, m), 1.48 (1H, dd, J=2.76 Hz and 12.3 Hz), 1.55 (1H, dt, J=3.8 Hz & 14.44 Hz), 2.12-2.19 (2H, m), 2.24-2.35 (3H, m), 2.42-2.50 (2H, m), 2.67-2.81 (4H, m), 2.96 (2H, t, J=7.48 Hz), 3.04 (1H, d, J=18.2 Hz), 3.78 (3H, s), 4.43 (1H, d, J=5.52 Hz), 4.59 (1H, s), 4.44 (1H, bd), 6.57 (1H, d, J=8.0 Hz), 6.69 (1H, d, J=8.0 Hz), 6.82 (2H, d, J=8.68 Hz), 7.15 (2H, d, J=8.68 Hz); ¹³C NMR, 400 MHz, (CDCl₃) δ 3.70, 3.76, 9.46, 23.05, 26.84, 30.14, 35.41, 36.87, 43.81, 51.18, 55.24, 55.59, 59.42, 82.43, 90.15, 113.94, 117.70, 119.88, 125.31, 128.05, 129.09, 132.48, 138.49, 143.25, 158.16, 171.81, 208.07. HRMS, m/z for ($C_{30}H_{34}NO_6$) [MH]⁺, calcd—504.2386. found—504.2479. Anal. ($C_{30}H_{33}NO_6 \cdot 2HCl \cdot H_2O$) C, H, N.

14β-(3'-methoxyphenylpropanoyl)-17-cyclopropylmethyl-78-dihydronoroxymorphinone White Solid; ¹H NMR (CDCl₃) δ 0.07-0.10 (2H, m), 0.48-0.50 (2H, m), 0.74-0.77 (1H, m), 1.46 (1H, dd, J=2.76 Hz and 12.3 Hz), 1.56 (1H, dt, J=3.8 Hz & 14.44 Hz), 2.14-2.20 (3H, m), 2.27-2.33 (3H, m), 2.38-2.52 (3H, m), 2.67 (1H, dd, J=4.56 Hz and 11.80 Hz), 2.77-2.82 (2H, m), 2.94-3.09 (3H, m), 3.83 (3H, s), 4.43 (1H, d, J=5.52 Hz), 4.58 (1H, s), 5.88 (1H, bd), 6.57 (1H, d, J=8.0 Hz), 6.70 (1H, d, J=8.0 Hz), 6.84-6.90 (2H, m), 7.18-7.21 (2H, m); ¹³C NMR, 400 MHz, (CDCl₃) δ 3.64, 3.82, 9.46, 23.09, 25.97, 26.94, 30.05, 35.14, 35.46, 43.80, 51.21, 55.21, 55.63, 59.43, 82.24, 90.15, 110.31, 117.84, 119.87, 120.45, 125.26, 127.61, 128.11, 128.81, 129.61, 138.59, 143.33, 157.41, 172.28, 208.55. HRMS, m/z for ($C_{30}H_{33}NO_6Na$) [MNa]⁺, calcd—526.22205. found—526.2237. Anal. ($C_{30}H_{33}NO_6 \cdot HCl \cdot 2.75H_2O$) C, H, N.

14β-(2'-methoxyphenylpropanoyl)-17-cyclopropylmethyl-7,8-dihydronoroxymorphinone White Solid; ¹H NMR (CDCl₃) δ 0.06-0.08 (2H, m), 0.47-0.50 (2H, m), 0.69-0.74 (1H, m), 1.47 (1H, dd, J=2.76 Hz and 12.3 Hz), 1.55 (1H, dt, J=3.8 Hz & 14.44 Hz), 2.11-2.18 (2H, m), 2.23-2.34 (3H, m), 2.42-2.50 (3H, m), 2.67 (1H, dd, J=4.72 Hz and 11.96 Hz), 2.74-2.86 (3H, m), 2.99 (2H, t, J=7.44 Hz), 3.04 (1H, d, J=18.44 Hz), 3.78 (3H, s), 4.43 (1H, d, J=5.48 Hz), 4.59 (1H, s), 6.01 (1H, bd), 6.57 (1H, d, J=8.0 Hz), 6.68 (1H, d, J=8.0 Hz), 6.71 (1H, dd, J=3.00 Hz and 7.12 Hz), 6.79-6.85 (2H, m), 7.19 (1H, m); $^{13}$C NMR, 400 MHz, (CDCl$_3$) δ 3.72, 3.75, 9.46, 23.05, 26.88, 30.07, 33.99, 35.35, 36.45, 43.83, 51.19, 55.12, 55.57, 59.39, 82.55, 90.09, 111.19, 114.44, 117.95, 119.89, 120.48, 125.18, 128.03, 129.53, 138.63, 142.07, 143.33, 159.75, 171.71, 208.51. HRMS, m/z for (C$_{30}$H$_{33}$NO$_6$Na) [MNa]+, calcd—526.22205. found—526.2218. Anal. (C$_{30}$H$_{33}$NO$_6$.HCl.1.5H$_2$O) C, H, N.

14β-(3'-methylphenylpropanoyl)-17-cyclopropylmethyl-7,8-dihydronoroxymorphinone (15)

White Solid; $^1$H NMR (CDCl$_3$) δ 0.06-0.09 (2H, m), 0.47-0.50 (2H, m), 0.70-0.74 (1H, m), 1.47 (1H, dd, J=2.76 Hz and 12.3 Hz), 1.55 (1H, dt, J=3.8 Hz & 14.44 Hz), 2.12-2.18 (2H, m), 2.24-2.35 (6H, m), 2.42-2.50 (2H, m), 2.67 (1H, dd, J=4.56 Hz and 11.80 Hz), 2.74-2.86 (3H, m), 2.99 (2H, t, J=7.96 Hz), 3.04 (1H, d, J=18.52 Hz), 4.43 (1H, d, J=5.48 Hz), 4.57 (1H, s), 5.91 (1H, bd), 6.57 (1H, d, J=8.0 Hz), 6.70 (1H, d, J=8.0 Hz), 7.01-7.06 (3H, m), 7.16-7.20 (1H, m); $^{13}$C NMR, 400 MHz, (CDCl$_3$) δ 3.71, 3.77, 9.47, 21.30, 23.06, 26.86, 30.08, 30.93, 35.32, 36.60, 43.83, 51.17, 55.59, 59.41, 82.48, 90.09, 117.88, 119.87, 125.11, 125.21, 127.07, 128.06, 128.44, 128.95, 138.11, 138.59, 140.40, 143.32, 171.80, 208.40. HRMS, m/z for (C$_{30}$H$_{33}$NO$_5$Na) [MNa]$^+$, calcd—510.2256. found—526.2306. Anal. (C$_{30}$H$_{33}$NO$_6$.2HCl.0.5H$_2$O) C, H, N.

14β-(4'-chlorophenylpropanoyl)-17-cyclopropylmethyl-7,8-dihydronoroxymorphinone (16)

White Solid; $^1$H NMR (CDCl$_3$) δ 0.04-0.08 (2H, m), 0.46-0.50 (2H, m), 0.64-0.67 (1H, m), 1.48 (1H, dd, J=2.76 Hz and 12.3 Hz), 1.57 (1H, dt, J=3.8 Hz & 14.44 Hz), 2.11-2.35 (4H, m), 2.39-2.51 (3H, m), 2.66 (1H, dd, J=4.56 Hz and 11.80 Hz), 2.72-2.86 (3H, m), 2.97 (2H, t, J=7.48 Hz), 3.04 (1H, d, J=18.2 Hz), 4.44 (1H, d, J=5.52 Hz), 4.62 (1H, s), 6.57 (1H, d, J=8.0 Hz), 6.70 (1H, d, J=8.0 Hz), 7.17 (2H, d, J=8.32 Hz), 7.24 (1H, d, J=8.32 Hz); $^{13}$C NMR, 400 MHz, (CDCl$_3$) δ 3.73, 9.42, 23.04, 26.98, 30.06, 30.26, 35.45, 36.41, 43.83, 51.23, 55.57, 59.41, 82.70, 90.08, 118.16, 119.96, 125.08, 127.93, 128.57, 129.58, 132.10, 138.73, 138.92, 143.35, 171.50, 208.55.

HRMS, m/z for (C$_{29}$H$_{30}$ClNO$_5$Na) [MNa]$^+$, calcd—530.1710. found—530.1707.

14β-(3'-chlorophenylpropanoyl)-17-cyclopropylmethyl-7,8-dihydronoroxymorphinone (17)

White Solid; $^1$H NMR (CDCl$_3$) δ 0.05-0.08 (2H, m), 0.46-0.50 (2H, m), 0.64-0.67 (1H, m), 1.48 (1H, dd, J=2.52 Hz and 12.4 Hz), 1.57 (1H, dt, J=3.8 Hz & 14.44 Hz), 2.14-2.27 (3H, m), 2.32-2.36 (2H, m), 2.38-2.49 (2H, m), 2.67 (1H, dd, J=4.56 Hz and 11.80 Hz), 2.74-2.86 (3H, m), 2.99 (2H, t, J=7.48 Hz), 3.04 (1H, d, J=18.2 Hz), 4.43 (1H, d, J=5.52 Hz), 4.61 (1H, s), 5.85 (1H, s), 6.57 (1H, d, J=8.0 Hz), 6.70 (1H, d, J=8.0 Hz), 7.12 (1H, dd, J=1.72 Hz and 7.12), 7.17-7.21 (3H, m); $^{13}$C NMR, 400 MHz, (CDCl$_3$) δ 3.72, 3.76, 9.44, 23.02, 26.94, 30.08, 30.57, 35.39, 36.21, 43.84, 51.22, 55.53, 59.38, 82.76, 90.11, 117.96, 119.93, 125.16, 126.43, 126.53, 127.95, 128.38, 129.75, 134.30, 138.63, 142.51, 143.30, 171.39, 208.23. HRMS, m/z for (C$_{29}$H$_{31}$ClNO$_5$) [MH]$^+$, calcd—508.1891. found—508.1917. Anal. (C$_{29}$H$_{30}$ClNO$_5$.2HCl.2H$_2$O) C, H, N.

14β-(4'-methylphenylpropanoyl)-17-cyclopropylmethyl-7,8-dihydronoroxymorphinone (18)

White Solid; $^1$H NMR (CDCl$_3$) δ 0.04-0.10 (2H, m), 0.45-0.51 (2H, m), 0.69-0.74 (1H, m), 1.47 (1H, dd, J=2.76 Hz and 12.3 Hz), 1.54 (1H, dt, J=3.8 Hz & 14.44 Hz), 2.11-2.18 (2H, m), 2.24-2.36 (6H, m), 2.42-2.53 (2H, m), 2.67 (1H, dd, J=4.56 Hz and 11.80 Hz), 2.73-2.86 (3H, m), 2.98 (2H, t, J=7.96 Hz), 3.04 (1H, d, J=18.52 Hz), 4.43 (1H, d, J=5.48 Hz), 4.59 (1H, s), 5.91 (1H, bd), 6.56 (1H, d, J=8.0 Hz), 6.70 (1H, d, J=8.0 Hz), 7.08 (2H, d, J=8.16 Hz), 7.13 (1H, d, J=8.16 Hz); $^{13}$C NMR, 400 MHz, (CDCl$_3$) δ 3.71, 3.75, 9.46, 20.90, 23.05, 26.89, 30.05, 30.58, 35.36, 36.70, 43.84, 51.19, 55.58, 59.41, 82.47, 90.06, 118.08, 119.90, 125.13, 128.04, 129.16, 135.87, 137.35, 138.71, 143.37, 171.86, 208.77. HRMS, m/z for (C$_{30}$H$_{33}$NO$_5$Na) [MNa]$^+$, calcd—510.2256. found—510.2265. Anal. (C$_{30}$H$_{33}$NO$_5$.2HCl.0.5H$_2$O) C, H, N.

14β-(2'-methylphenylpropanoyl)-17-cyclopropylmethyl-7,8-dihydronoroxymorphinone (19)

White Solid; $^1$H NMR (CDCl$_3$) δ 0.06-0.10 (2H, m), 0.47-0.50 (2H, m), 0.73-0.76 (1H, m), 1.48 (1H, dd, J=2.76 Hz and 12.3 Hz), 1.58 (1H, dt, J=3.8 Hz & 14.44 Hz), 2.14-2.23 (2H, m), 2.29-2.48 (5H, m), 2.50-2.54 (3H, m), 2.68 (1H, dd, J=4.56 Hz and 11.80 Hz), 2.75-2.84 (3H, m), 3.00 (2H, m), 3.05 (1H, d, J=18.52 Hz), 4.44 (1H, d, J=5.48 Hz), 4.60 (1H, s), 6.00 (1H, bd), 6.58 (1H, d, J=8.0 Hz), 6.71 (1H, d, J=8.0 Hz), 7.10-7.21 (4H, m); $^{13}$C NMR, 400 MHz, (CDCl$_3$) δ 3.66, 3.83, 9.47, 19.26, 23.07, 26.99, 28.36, 30.10, 35.47, 43.84, 51.24, 55.65, 59.46, 82.51, 90.13, 117.98, 119.91, 125.19, 126.11, 126.46, 128.01, 128.24, 130.33, 135.83, 138.53, 138.64, 143.34, 171.94, 208.44. HRMS, m/z for (C$_{30}$H$_{33}$NO$_5$Na) [MNa]$^+$, calcd—510.2256. found—510.2251. Anal. (C$_{30}$H$_{33}$NO$_5$.2HCl) C, H, N.

14β-(2'-fluorophenylpropanoyl)-17-cyclopropylmethyl-7,8-dihydronoroxymorphinone (20)

White solid. R$_f$ 0.28 (at 30% EtOAc/Hexane, 0.5% NH$_3$), $^1$H NMR (400 MHz, CDCl$_3$) δ 0.04-0.06 (2H, d, J=8.0 Hz), 0.47-0.49 (2H, d, J=8.0 Hz), 0.85-0.89 (1H, m), 1.48-1.50 (1H, d, J=9.7 Hz), 1.61-1.63 (1H, t, J=14.5 Hz), 2.04-2.50 (7H, m), 2.66-2.69 (1H, m), 2.76-2.85 (3H, m), 3.01-3.10 (3H, m), 4.42-4.44 (1H, d, J=5.5 Hz), 4.66 (1H, s), 6.20 (1H, brs), 6.55-6.57 (2H, d, J=8.0 Hz), 6.71-6.73 (2H, d, J=8.0 Hz), 6.99-7.08 (2H, m), 7.18-7.20 (1H, m), 7.25-7.26 (1H, m); $^{13}$C NMR (100.6 MHz, CDCl$_3$) δ 3.7, 9.4, 20.5, 23.0, 24.4, 26.9, 30.0, 35.2, 35.4, 43.8, 51.1, 55.5, 59.4, 82.7, 90.0, 115.2, 115.4, 118.0, 119.8, 124.1, 124.9, 127.2, 128.0, 128.1, 130.3, 138.8, 143.4, 171.6, 208.8; ESIMS m/z: 492.220 [M+1]$^+$.

14β-(4'-fluorophenylpropanoyl)-17-cyclopropylmethyl-7,8-dihydronoroxymorphinone (21)

White solid. R$_f$ 0.30 (at 30% EtOAc/Hexane, 0.5% NH$_3$), $^1$H NMR (400 MHz, CDCl$_3$) δ 0.04-0.06 (2H, d, J=8.0 Hz), 0.46-0.48 (2H, d, J=8.0 Hz), 0.67 (1H, m), 1.48-1.50 (1H, d, J=9.7 Hz), 1.60-1.63 (1H, t, J=14.5 Hz), 2.13-2.21 (3H, m), 2.22-2.32 (1H, m), 2.34-2.49 (3H, m), 2.65-2.68 (1H, m), 2.72-2.86 (3H, m), 2.97-3.01 (2H, t, J=16 Hz), 3.04-3.08 (1H, d, J=16.0 Hz), 4.43-4.45 (1H, d, J=5.5 Hz), 4.63 (1H, s), 6.56-6.58 (2H, d, J=8.0 Hz), 6.70-6.72 (2H, d, J=8.0 Hz), 6.96-6.98 (2H, d, J=8.0 Hz), 7.20-7.22 (2H, d, J=8.0 Hz); $^{13}$C NMR (100.6 MHz, CDCl$_3$) δ 3.7, 9.4, 22.9, 26.9, 14.1, 30.1, 35.4, 36.7, 43.8, 51.2, 52.5, 55.4, 59.3, 60.4, 82.6, 90.0, 115.1, 115.3, 118.2, 119.9, 124.9, 127.9, 129.6, 136.1, 138.8, 143.4, 160.2, 162.6, 171.7, 209.0; ESIMS m/z: 492.219 [M+1]$^+$.

14β-(2',4'-difluorophenylpropanoyl)-17-cyclopropylmethyl-7,8-dihydronoroxymorphinone (22)

White solid. R$_f$ 0.37 (at 30% EtOAc/Hexane, 0.5% NH$_3$), $^1$H NMR (400 MHz, CDCl$_3$) δ 0.04-0.06 (2H, d, J=8.0 Hz), 0.45-0.47 (2H, d, J=8.0 Hz), 0.66 (1H, m), 1.48-1.50 (1H, d, J=9.7 Hz), 1.61-1.65 (1H, t, J=14.5 Hz), 2.12-2.15 (1H, t, J=8.0 Hz), 2.22-2.34 (3H, m), 2.42-2.53 (3H m), 2.66-2.70 (1H, m), 2.75-2.82 (3H, m), 2.97-3.03 (3H, m), 4.42-4.43 (1H, d, J=5.5 Hz), 4.67 (1H, s), 6.56-6.58 (2H, d, J=8.0 Hz), 6.70-6.72 (2H, d, J=8.0 Hz), 6.73-6.81 (2H, m), 7.21-7.25 (1H, d, J=8.0 Hz); $^{13}$C NMR (100.6 MHz, CDCl$_3$) 3.7, 9.4, 14.1, 22.9, 23.9, 27.0, 29.9, 35.4, 43.8, 51.2, 55.5, 59.3, 60.4, 82.7, 90.0, 103.9, 111.1, 118.2, 119.9, 123.2, 124.9, 127.9, 130.9, 131.1, 138.7, 143.3, 171.5, 209.1; ESIMS m/z: 510.209 [M+1]$^+$.

14β-(4'-bromophenylpropanoyl)-17-cyclopropylmethyl-7,8-dihydronoroxymorphinone (23)

White solid. R$_f$ 0.33 (at 30% EtOAc/Hexane, 0.5% NH$_3$), $^1$H NMR (400 MHz, CDCl$_3$) δ 0.03-0.05 (2H, d, J=8.0 Hz), 0.44-0.48 (2H, t, J=8.0 Hz), 0.64 (1H, m), 1.46-1.48 (1H, d, J=9.7 Hz), 1.60-1.64 (1H, t, J=14.5 Hz), 2.11-2.25 (3H, m), 2.30-2.34 (1H, m), 2.40-2.48 (3H, m), 2.65-2.68 (1H, m), 2.72-2.85 (3H, m), 2.94-2.98 (2H, t, J=8.0 Hz), 3.03-3.07 (1H, 16.0 Hz), 4.43-4.44 (1H, d, J=5.5 Hz), 4.65 (1H, s), 6.55-6.57 (2H, d, J=8.0 Hz), 6.70-6.72 (2H, d, J=8.0 Hz), 7.11-7.13 (2H, d, J=8.0 Hz), 7.37-7.39 (2H, d, J=8.0 Hz); $^{13}$C NMR (100.6 MHz, CDCl$_3$) δ 3.7, 4.2, 9.4, 14.1, 22.9, 26.9, 28.8, 29.9, 35.4, 36.3, 43.8, 51.2, 55.4, 59.3, 60.4, 82.7, 89.9, 117.5, 119.8, 119.9, 124.9, 128.7, 130.1, 131.4, 138.8, 139.4, 143.4, 171.6, 209.1. ESIMS m/z: 552. 138 [M+1]$^+$.

14β-(2'-bromophenylpropanoyl)-17-cyclopropylmethyl-7,8-dihydronoroxymorphinone (24)

White solid. R$_f$ 0.30 (at 30% EtOAc/Hexane, 0.5% NH$_3$), $^1$H NMR (400 MHz, CDCl$_3$) δ 0.04-0.08 (2H, t, J=8.0 Hz), 0.46-0.48 (2H, d, J=8.0 Hz), 0.73 (1H, m), 1.47-1.51 (1H, d, J=9.7 Hz), 1.61-1.64 (1H, t, J=14.5 Hz), 2.12-2.24 (2H, m), 2.26-2.35 (2H, m), 2.41-2.53 (3H, m), 2.67-2.71 (1H, m), 2.77-2.85 (3H, m), 3.04-3.08 (1H, d, J=16.0 Hz), 3.11-3.19 (2H, m), 4.44-4.45 (1H, d, J=5.5 Hz), 4.66 (1H, s), 6.56-6.58 (2H, d, J=8.0 Hz), 6.70-6.72 (2H, d, J=8.0 Hz), 7.07-7.09 (1H, t, J=4.0 Hz), 7.23-7.31 (2H, m), 7.52-7.54 (1H, d, J=8.0 Hz); $^{13}$C NMR (100.6 MHz, CDCl$_3$) δ 3.7, 3.8, 9.4, 14.1, 23.0, 27.0, 30.0, 35.1, 35.5, 43.8, 51.2, 55.5, 59.4, 60.4, 82.6, 90.0, 118.2, 119.9, 124.3, 127.5, 128.0, 128.1, 130.1, 132.9, 138.7, 139.6, 143.4, 171.6, 209.14; ESIMS m/z: 552.141 [M+1]$^+$.

14β-(2'-chlorophenylpropanoyl)-17-cyclopropylmethyl-7,8 dihydronoroxymorphinone (25)

White solid. R$_f$ 0.30 (at 30% EtOAc/Hexane, 0.5% NH$_3$), $^1$H NMR (400 MHz, CDCl$_3$) δ 0.05-0.07 (2H, d, J=8.0 Hz), 0.46-0.48 (2H, d, J=8.0 Hz), 0.72 (1H, m), 1.48-1.51 (1H, d, J=9.7 Hz), 1.57-1.61 (1H, t, J=14.5 Hz), 2.12-2.32 (4H, m), 2.41-2.52 (4H, m), 2.67-2.70 (1H, m), 2.77-2.85 (3H, m), 3.04-3.08 (1H, d, J=16.0 Hz), 3.11-3.19 (2H, m), 4.43-4.45 (1H, d, J=5.5 Hz), 4.65 (1H, s), 6.56-6.58 (2H, d, J=8.0 Hz), 6.70-6.72 (2H, d, J=8.0 Hz), 7.15-7.19 (2H, m), 7.25-7.29 (1H, d, J=4.0 Hz) 7.30-7.35 (1H, d, J=4.0 Hz); $^{13}$C NMR (100.6 MHz, CDCl$_3$) δ 3.8, 9.4, 14.1, 25.5, 27.0, 28.9, 29.9, 34.9, 35.4, 43.8, 51.2, 55.5, 59.4, 82.6, 90.0, 118.2, 119.9, 124.9, 126.9, 127.8, 128.0, 129.5, 130.1, 133.8, 138.0, 138.8, 143.4, 171.6, 209.2; ESIMS m/z: 508.189 [M+1]$^+$.

14β-(2',4'-dichlorophenylpropanoyl)-17-cyclopropylmethyl-7,8-dihydronoroxymorphinone (26)

White solid. R$_f$ 0.39 (at 30% EtOAc/Hexane, 0.5% NH$_3$), $^1$H NMR (400 MHz, CDCl$_3$) δ $^1$H NMR (400 MHz, CDCl$_3$) δ 0.04-0.06 (2H, d, J=8.0 Hz), 0.45-0.47 (2H, d, J=8.0 Hz), 0.67 (1H, m), 1.48-1.50 (1H, d, J=9.7 Hz), 1.62-1.66 (1H, t, J=14.5 Hz), 2.09-2.12 (1H, t, J=8.0 Hz), 2.22-2.34 (3H, m), 2.42-2.54 (3H m), 2.66-2.71 (1H, m), 2.77-2.87 (3H, m), 3.04-3.08 (1H, d, J=16.0 Hz), 3.06-3.12 (2H, m), 4.42-4.43 (1H, d, J=5.5 Hz), 4.68 (1H, s), 6.56-6.58 (2H, d, J=8.0 Hz), 6.70-6.72 (2H, d, J=8.0 Hz), 7.15-7.17 (1H, d, J=8.0 Hz), 7.22-7.25 (1H, d, J=8.0 Hz), 7.36 (1H, s); $^{13}$C NMR (100.6 MHz, CDCl$_3$) δ 3.7, 9.4, 14.1, 22.9, 27.0, 28.3, 29.9, 34.6, 35.5, 43.8, 51.2, 55.5, 59.3, 60.4, 82.8, 90.0, 118.3, 119.9, 124.9, 17.9, 129.2, 131.1, 132.7, 134.4, 136.6, 138.8, 143.4, 171.4, 209.19; ESIMS m/z: 542.150 [M+1]$^+$.

14β-phenylbutanoyl-17-cyclopropylmethyl-7,8-dihydronoroxymorphinone (27)

White Solid; $^1$H NMR (CDCl$_3$) δ 0.03-0.07 (2H, m), 0.43-0.49 (2H, m), 0.72-0.76 (1H, m), 1.50 (1H, dd, J=2.52 Hz & 12.28 Hz), 1.59 (1H, dt, J=3.72 Hz & 14.44 Hz), 2.04-2.08 (3H, m), 2.12 (1H, dt, J=3.84 Hz & 12.08 Hz), 2.26-2.36 (3H, m), 2.42-2.59 (4H, m), 2.66-2.77 (3H, m), 2.81-2.86 (1H, m), 3.06 (1H, d, J=18.52 Hz), 4.47 (1H, d, J=5.48 Hz), 4.66 (1H, s), 5.90 (1H, bd), 6.58 (1H, d, J=8.16 Hz), 6.71 (1H, d, J=8.16 Hz), 7.18-7.22 (3H, m), 7.28-7.31 (2H, m); $^{13}$C NMR, 400 MHz, (CDCl$_3$) δ 3.68, 3.81, 9.40, 23.03, 26.58, 26.97, 30.05, 34.70, 35.11, 35.66, 43.85, 51.27, 55.65, 59.52, 82.30, 90.20, 117.98, 119.95, 125.24, 125.99, 128.04, 128.38, 138.65, 141.35, 143.34, 172.38, 208.44. HRMS, m/z for (C$_{30}$H$_{34}$NO$_5$) [MH]$^+$, calcd—488.2437. found—488.2466. Anal. (C$_{29}$H$_{31}$NO$_5$·HCl·H$_2$O) C, H, N.

14β-phenylpropanoyl-17-cyclopropylmethyl-4,5α-epoxy-6-methylenemorphinan-3,14-diol White solid. R$_f$ 0.42 (at 30% EtOAc/Hexane, 0.5% NH$_3$), $^1$H NMR (400 MHz, CDCl$_3$) δ $^1$H NMR (400 MHz, CDCl$_3$) δ 0.04-0.06 (2H, d, J=8.0 Hz), 0.45-0.47 (2H, d, J=8.0 Hz), 0.66-0.72 (1H, m), 1.16-1.31 (2H, m), 1.41-1.47 (2H, m), 2.08 (1H, brs), 2.12-2.15 (2H, m), 2.25-2.30 (2H, m), 2.38-2.53 (2H, m), 2.68-2.78 (3H, m), 2.99-3.05 (2H, m), 4.36-4.37 (1H, d, J=5.0 Hz), 4.84 (1H, s), 4.96 (1H, s), 6.52-6.54 (2H, d, J=8.0 Hz), 6.65-6.67 (2H, d, J=8.0 Hz), 7.24-7.31 (5H, m); $^{13}$C NMR (100.6 MHz, CDCl$_3$) δ 3.6, 3.7, 20.7, 23.0, 27.4, 27.5, 28.3, 30.0, 31.0, 36.8, 44.4, 48.8, 53.4, 55.9, 59.4, 83.8, 89.5, 112.0, 116.7, 118.8, 125.6, 126.1, 128.2, 130.0, 138.9, 140.7, 143.0, 144.4, 171.7; ESIMS m/z: 472.259 [M+1]$^+$.

14β-phenylpropanoyl-17-cyclopropylmethyl-4,5α-epoxy-morphinan-3,6β,14-triol (29)

White solid, Rf 0.22 (30% EtOAc/Hexane, 0.5% NH$_3$), $^1$H NMR (500 MHz, CDCl$_3$) δ 0.01-0.03 (2H, d, J=8.2 Hz), 0.43-0.45 (2H, d, J=8.2 Hz), 0.67-69 (1H, m), 1.26-1.38 (2H, m), 1.54-1.618 (2H, m), 2.03-2.09 (1H, m), 2.23-2.34 (3H, m), 2.44-2.46 (1H, d, J=10.0 Hz), 2.52-2.54 (1H, d, J=10.0 Hz), 2.60-2.63 (1H, m), 2.66-2.78 (2H, m), 2.95-2.99 (1H, d, J=20.0 Hz) 2.99-3.03 (2H, m), 3.50-3.55 (1H, q), 4.35-4.36 (1H, d, J=5.0 Hz), 4.46-4.47 (1H, d, J=5.0 Hz), 6.54-6.56 (2H, d, J=8.0 Hz), 6.68-6.70 (2H, d, J=8.0 Hz), 7.18-7.31 (5H, m); $^{13}$C NMR (125.7 MHz, CDCl$_3$) δ 3.6, 3.7, 23.0, 25.5, 25.6, 29.8, 31.0, 36.8, 43.9, 48.0, 55.6, 59.4, 72.8, 82.9, 96.1, 117.4, 119.3, 125.2, 126.1, 128.2, 128.4, 130.9, 139.5, 140.7, 141.6, 171.6; ESIMS m/z: 476.253[M+1]$^+$.

14β-i-hexanoyl-17-cyclopropylmethyl-7,8-dihydronoroxymorphinone (30)

White solid. R$_f$ 0.29 (at 30% EtOAc/Hexane, 0.5% NH$_3$), $^1$H NMR (400 MHz, CDCl$_3$) δ 0.04-0.07 (2H, t, J=8.0 Hz), 0.46-0.48 (2H, d, J=8.0 Hz), 0.74 (1H, m), 0.91-0.93 (6H, d, J=9.7 Hz), 1.49-1.68 (5H, m), 2.12-2.15 (1H, t, J=14.5 Hz), 2.25-2.35 (3H, m), 2.41-2.50 (4H, m), 2.52-2.72 (2H, m), 2.81-2.85 (1H, m), 3.04-3.08 (1H, d, J=16.0 Hz), 4.44-4.46 (1H, d, J=5.5 Hz), 4.46 (1H, s), 6.56-6.58 (2H, d, J=8.0 Hz), 6.71-6.73 (2H, d, J=8.0 Hz); $^{13}$C NMR (100.6 MHz, CDCl$_3$) δ 3.6, 3.8, 9.3, 22.2, 22.3, 22.9, 26.9, 27.5, 30.0, 33.5, 33.9, 35.6, 43.8, 51.2, 55.5, 59.4, 82.1, 90.1, 118.0, 119.9, 125.1, 128.1, 138.6, 143.3, 173.0, 209.0; ESIMS m/z: 440.246 [M+1]$^+$.

14β-phenylpropyl-17-cyclopropylmethyl-4,5α-epoxy-morphinan-3,6β,14-triol (31)

White solid. R$_f$ 0.21 (at 30% EtOAc/Hexane, 0.5% NH$_3$), $^1$H NMR (400 MHz, CDCl$_3$) δ $^1$H NMR (400 MHz, CDCl$_3$) δ 0.05-0.07 (2H, d, J=8.0 Hz), 0.42-0.44 (2H, d, J=8.0 Hz), 0.67-0.72 (1H, m), 1.29-1.32 (1H, d, J=12.0 Hz), 1.33-1.38 (1H, m), 1.78-1.89 (2H, m), 1.93-1.97 (2H, m), 2.06-2.04 (1H, m), 2.28-2.30 (2H, d, J=8.0 Hz), 2.34-2.36 (1H, d, J=8.0 Hz), 2.51-2.58 (1H, m), 2.64-2.68 (1H, m), 2.75-279 (2H, t, J=8.0 Hz), 3.04-3.09 (1H, d, J=20.0 Hz), 3.29-3.34 (1H, q), 3.40-3.41 (1H, d, J=4.0 Hz), 3.55-3.59 (1H, q), 3.65-3.70 (1H, q), 4.54-4.56 (1H, d, J=8.0 Hz), 6.51-6.53 (2H, d, J=8.0 Hz), 6.67-6.69 (2H, d, J=8.0 Hz), 7.17-7.29 (5H, m); $^{13}$C NMR (100.6 MHz, CDCl$_3$) δ 3.6, 3.7, 9.1, 23.4, 23.7, 24.8, 30.0, 31.8, 32.7, 40.7, 44.6, 47.8, 55.9, 58.5, 60.3, 72.0, 75.4, 95.8, 116.8, 118.9, 125.6, 128.4, 131.8, 139.0, 142.3, 142.4;
ESIMS m/z: 462.274 [M+1]$^+$.

14β-phenylpropyl-17-cyclopropylmethyl-4,5α-epoxy-6-methylenemorphinan-3,14-diol (32)

White solid. R$_f$ 0.56 (30% EtOAc/Hexane, 0.5% NH$_3$) $^1$H NMR (400 MHz, CDCl$_3$) δ $^1$H NMR (400 MHz, CDCl$_3$) δ 0.06-0.08 (2H, d, J=8.0 Hz), 0.43-0.45 (2H, d, J=8.0 Hz), 0.68-0.73 (1H, m), 1.10-1.18 (1H, m), 1.23-1.38 (1H, m), 1.55-1.57 (1H, m), 1.75-1.73 (1H, d, J=12.0 Hz), 1.95-2.08 (5H, m), 2.62-2.78 (3H, m), 2.45-2.67 (2H, m), 2.76-2.80 (2H, t, J=8.0 Hz), 3.03-3.08 (1H, d, J=20.0 Hz), 3.28-3.39 (1H, q), 3.39-3.40 (1H, brs), 3.65-3.68 (1H, q), 4.83 (1H, s), 5.02 (1H, s), 5.23 (1H, s), 6.51-6.53 (2H, d, J=8.0 Hz), 6.65-6.67 (2H, d, J=8.0 Hz), 7.17-7.30 (5H, m); ESIMS m/z: 458.279 [M+1]$^+$.

Evaluation:
Binding Affinities to Human Opioid Receptors Transfected into Chinese Hamster Ovary (CHO) Cells.

Binding to cell membranes was examined as described previously (Adapa and Toll, 1997; Toll et al., 1998). Cells were removed from the plates by scraping with a rubber policeman, homogenized in Tris buffer using a Polytron homogenizer, then centrifuged once and washed by an additional centrifugation at 40,000×g for 15 min. The pellet was resuspended in 50 mM Tris, pH 7.5, and the suspension incubated with [$^3$H]N/OFQ, [$^3$H]DAMGO or [$^3$H]U69593, for binding to NOP, MOP and KOP respectively, in a total volume of 1.0 ml, in a 96-well format, for 120 min at 25° C. Samples were filtered over glass fiber filters by using a Wallac cell harvester. For the NOP binding experiments, 1 mg/ml bovine serum albumin was used to prevent absorption of the ligand to the glass tubes, and filters were soaked in 0.1% polyethyleneimine (PEI) to prevent adsorption to the glass fiber filters, thus lowering nonspecific binding. For routine experiments, membranes were incubated in triplicate with the test compounds at concentrations ranging from $10^{-5}$ to $10^{-10}$ M. The experiment was repeated using concentrations in half log units around the IC$_{50}$ value. A standard compound was run concurrently in each experiment for quality control. After the incubation, samples were filtered and dried overnight before radioactivity levels were determined. Nonspecific binding was determined by using 1.0 µM of the unlabeled counterpart of each radioligand. IC$_{50}$ values and slope factors were determined by the curve-fitting program Prism. Ki may be calculated using the formula Ki=IC$_{50}$/(1+[L]/Kd) (Cheng and Prusoff, 1973).

[$^{35}$S]GTPγS binding was conducted basically as described by Traynor and Nahorski (Traynor et al., 1995). Cells were scraped from tissue culture dishes into 20 mM Hepes, 1 mM EDTA, then centrifuged at 500×g for 10 min. Cells were resuspended in this buffer and homogenized using a Polytron Homogenizer. The homogenate was centrifuged at 27,000×g for 15 min, and the pellet re suspended in Buffer A, containing: 20 mM Hepes, 10 mM MgCl$_2$, 100 mM NaCl, pH 7.4. The suspension was re centrifuged at 27,000×g and suspended once more in Buffer A. For the binding assay, membranes (8-15 µg protein) were incubated with [$^{35}$S]GTPγS (50 pM), GDP (10 µM), and the appropriate compound, in a total volume of 1.0 ml, for 60 min at 25'C. Samples were filtered over glass fiber filters and counted as described for the binding assays. Statistical analysis was conducted using the program Prism®.

TABLE 1

| Compound | Ki/nM | | | % stim MOP | % stim NOP |
|---|---|---|---|---|---|
| | NOP | MOP | KOP | | |
| 1 | 127 ± 17 | 0.86 ± 0.18 | 1.14 ± 0.46 | 32 | 28 |
| 2 | 36.3 ± 4.2 | 1.87 ± 0.09 | 1.56 ± 0.28 | 35 | 22 |
| 3 | 44.1 ± 3.1 | 3.59 ± 0.86 | 1.69 ± 1.2 | 42 | 21 |
| 4 | 49.9 ± 3.5 | 1.91 ± 0.51 | 2.8 ± 0.91 | 40 | 59 |
| 5 | 50.1 ± 2.7 | 1.10 ± 0.08 | 1.44 ± 0.33 | 11 | 36 |
| 6 | 94.3 ± 28 | 0.99 ± 0.35 | 1.20 ± 0.42 | 12 | 44 |
| 7 | 62.3 ± 4.9 | 3.77 ± 0.9 | 3.52 ± 0.9 | 37 | 41 |
| 8 | 69.7 ± 2.4 | 2.59 ± 1.1 | 4.55 ± 0.7 | 28 | 15 |
| 9 | 51.3 ± 14 | 1.78 ± 0.03 | 3.95 ± 0.59 | 8.2 | 19 |
| 10 | 32.6 ± 2.3 | 4.66 ± 1.8 | 1.34 ± 0.5 | 39 | 50 |
| 11 | 14.78 ± 0.94 | 0.86 ± 0.23 | 10.5 ± 0.17 | 18 | 34 |
| 12 | 766.13 ± 176.7 | 0.91 ± 0.12 | 1.96 ± 0.04 | NS | 52 |
| 13 | 153.87 ± 11.52 | 1.14 ± 0.18 | 1.24 ± 0.15 | NS | 46 |
| 14 | 119.62 ± 20.5 | 1.67 ± 0.42 | 1.24 ± 0.11 | NS | 56 |
| 15 | 37.68 ± 2.6 | 0.91 ± 0.1 | 1.56 ± 0.2 | 23 | NT |
| 16 | 45.22 ± 17.5 | 0.54 ± 0.11 | 1.34 ± 0.12 | 21 | 41 |
| 17 | 27.0 ± 4.9 | 0.39 ± 0.07 | 0.74 ± 0.05 | 26 | 22 |
| 18 | 35.77 ± 1.6 | 0.78 ± 0.22 | 1.06 ± 0.4 | 25 | 63 |
| 19 | 12.1 ± 2.7 | 0.56 ± 0.11 | 0.64 ± 0.1 | 48 | 33 |
| Naltrexone | >10K | 0.66 ± 0.10 | 1.1 ± 0.22 | NS | NS |
| Buprenorphine | 77.4 ± 16 | 1.5 ± 0.8 | 2.5 ± 1.2 | | |

NS: No stimulation;
NT: Not Tested

Compounds 11, 12, 13, 14, 16 and 17 were evaluated at the KOPr and showed no stimulation of the receptor.

Figure 1B:
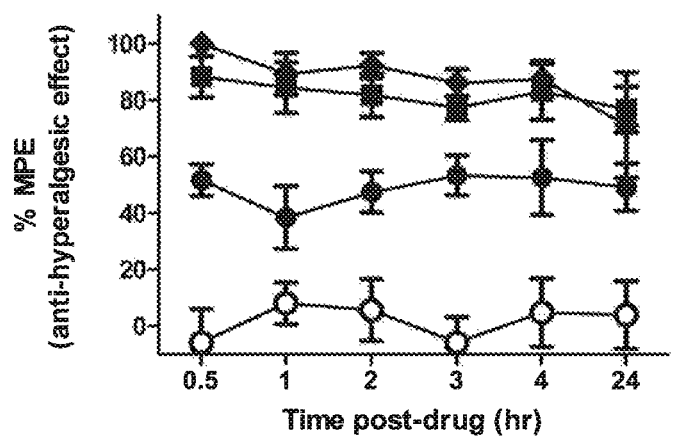
Figure 2:
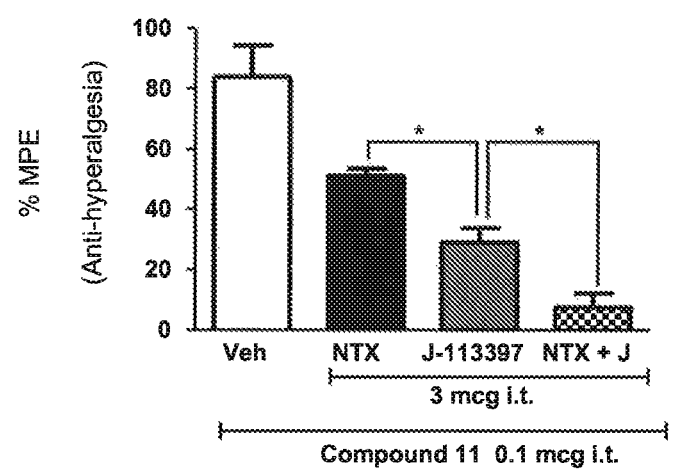
FIG. 2 shows the effect of pretreatment with MOP and NOP receptor antagonists on 11 induced reversal of thermal hyperalgesia.

Compound 11 was tested for its effect on carrageenan-induced thermal hyperalgesia measured by paw withdrawal latency (FIG. 1a) and anti-hyperalgesic effect (FIG. 1b). 11 is efficacious and long acting in this assay. FIG. 2 shows the effect of pretreatment with MOP and NOP receptor antagonists on 11-induced reversal of thermal hyperalgesia. Both the MOP receptor antagonist naltrexone and the NOP receptor antagonist J113397 could partially reverse the activity of compound 11, confirming that compound 11 is acting through both MOP and NOP receptors.

In pilot experiments, subcutaneous (s.c.) administration of compound 11 (0.001-0.01 mg/kg) dose-dependently produced long lasting antinociception (~24 hours) against acute noxious stimulus (50° C. water) in rhesus monkeys. At a dose (0.01 mg/kg s.c.) of 11 that produced full antinociceptive effects, we found that 11 did not affect the physiological functions of monkeys, i.e., no respiratory depression and no bradycardia and hypotension. In the operant responding assay, monkeys did not self-administer 11, indicating lack of potential abuse liability. Intrathecal administration of 11 at 3 μg produced full antinociceptive effects that lasted for 24 hours without eliciting scratching responses (a side effect of standard mu opioid analgesics). These subjects did not show any signs of sedation during this test period. These findings illustrate the safe and favorable profile of 11.

REFERENCES

A number of publications are cited herein in order more fully to describe and disclose the invention and the state of the art to which the invention pertains. Full citations for these references are provided below. Each of these references is incorporated herein by reference in its entirety in the present disclosure, to the same extent as if each individual reference was specifically and individually indicated to be incorporated by reference.

Beardsley et al, *Psychopharmacol.* 2005, 183(1): 118-126.
Champion et al., *Am. J. Physiol: Endocrinol Metab.* 1997, 273, E214-E219.
Florin et al., *Eur. J. Pharmacol.* 1996, 317, 9-13.
Goeldner et al. *Neurobiol. Learn. Mem.* 2009, 91, 393-401.
Gumusel et al., *Life Sci.* 1997, 60, 141-145.
Jenck et al., *Proc. Natl. Acad. Sci.* 1997, 94, 14854-14858.
Kovacs et al, *Alcohol Clin. Exp. Res.* 2005, 29(5), 730-738.
Manabe et al. *Nature* 1998, 394, 577-581.
McLaughlin et al, *J. Neurosci.* 2003, 23(13): 5674-5683.
Mogil et al. *Neuroscience* 1996, 75, 333-337.
Mustazza and Bastanzio, *Medicinal Research Reviews* 2011, 31, 605-648.
Pomonis et al., *Neuro Report* 1996, 8, 369-371.
Redila and Chavkin, *Psychopharmacol.* 2008, 200(1): 59-70.
Reinsceid et al., *Science* 1995, 270, 792-794.
Ueda et al., *Neuroscience Lett.* 1997, 237, 136-138.
Van't Veer and Carlezon Jr, *Psychopharmacology* 2013, 229(3), 435-52.
Walker and Koob, *Neuropsychopharmacol.* 2007, 33(3): 643-652.
Whiteside and Kyle in Research and Development of Opioid-Related Ligands, ACS Symposium Series 1131, 2013, pp 327-368.

The invention claimed is:

1. A compound selected from compounds of formula 2

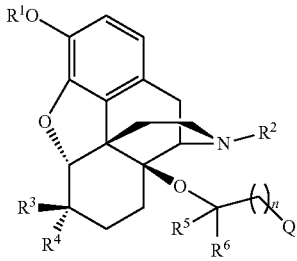

wherein:
$R^1$ is H or methyl;
$R^2$ is $C_{3-5}$ alkyl, $C_{3-5}$ alkenyl or $C_{3-5}$ cycloalkyl-$C_{1-2}$ alkyl;
$R^3$ and $R^4$ are together =O;
$R^5$ and $R^6$ are together =O;
n is 1-4; and Q is branched alkyl of 3-6 carbon atoms or branched alkenyl of 3-6 carbon atoms, phenyl, or heteroaryl of 5-6 ring atoms with at least one atom selected from N, O or S;
wherein each phenyl or heteroaryl is optionally substituted with one or two $R^Q$ substituents, wherein each $R^Q$ is independently selected from the group consisting of halogen, $C_{1-3}$ alkyl, $CF_3$, OH, $C_{1-3}$ alkyloxy, —$NH_2$, —$NHR^7$, and $NR^7R^8$, wherein $R^7$ and $R^8$ are independently $C_{1-3}$ alkyl; or two adjacent $R^Q$ together form —O—$(CH_2)_m$—O—, wherein m is 1, 2 or 3;
with the proviso that:
when n is 1, Q is not unsubstituted phenyl;
or a pharmaceutically acceptable salt, hydrate, and/or solvate thereof.

2. The compound of claim 1, wherein $R^1$ is H.
3. The compound of claim 1, wherein $R^2$ is cyclopropylmethyl.
4. The compound of claim 1, wherein n is 1, 2 or 3.
5. The compound of claim 1, wherein n is 1 or 2.
6. The compound of claim 1, wherein n is 2.
7. The compound of claim 1, wherein Q is phenyl.
8. The compound of claim 1, wherein Q is phenyl substituted with one or two $R^Q$ substituents, wherein each $R^Q$ is independently selected from the group consisting of halogen, $C_{1-3}$ alkyl, $CF_3$, hydroxyl, $C_{1-3}$ alkyloxy, —$NHR^7$, and $NR^7R^8$, wherein $R^7$ and $R^8$ are independently $C_{1-3}$ alkyl; or two adjacent $R^Q$ together form —O—$(CH_2)_m$—O—, wherein m is 1, 2 or 3.
9. The compound of claim 8, wherein Q is phenyl substituted with one $R^Q$ substituent.
10. The compound of claim 8, wherein $R^Q$ is selected from the group consisting of halogen, $C_{1-3}$ alkyl, $CF_3$, OH, and $C_{1-3}$ alkyloxy, or two adjacent $R^Q$ together form —O—$(CH_2)$—O—.
11. The compound of claim 8, wherein $R^Q$ is selected from the group consisting of F, Cl, Me, $CF_3$, OMe, and OH.
12. The compound of claim 1, wherein $R^1$ is H, $R^2$ is cyclopropylmethyl, n is 2, and Q is phenyl.
13. A compound selected from the group consisting of:

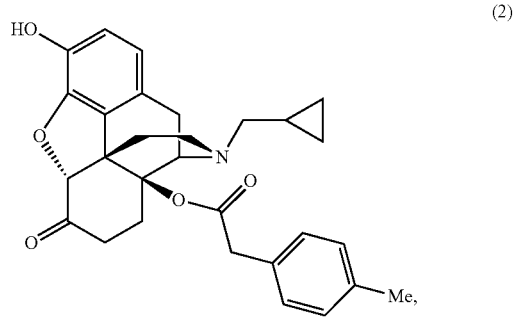

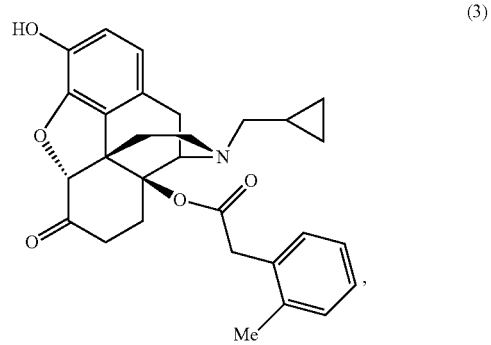

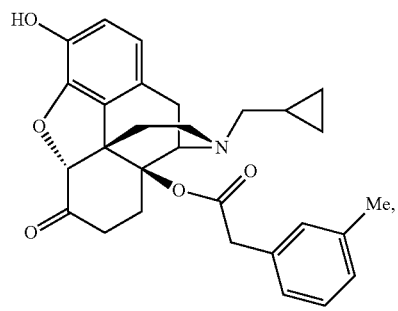
(4)
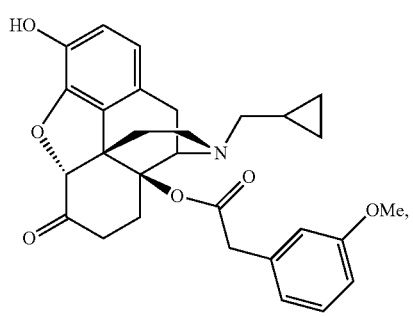
(5)
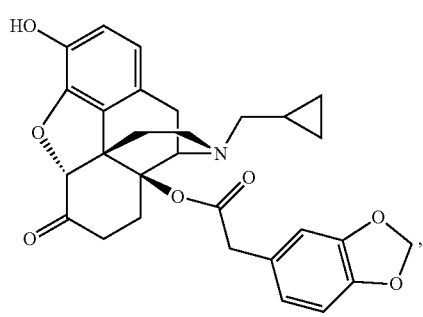
(6)
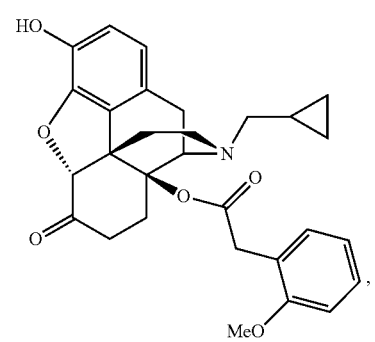
(7)
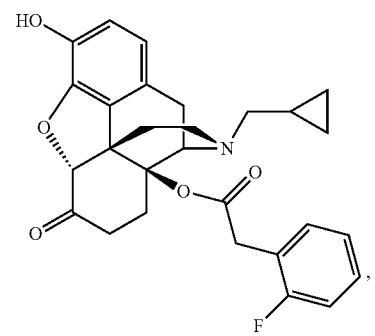
(8)
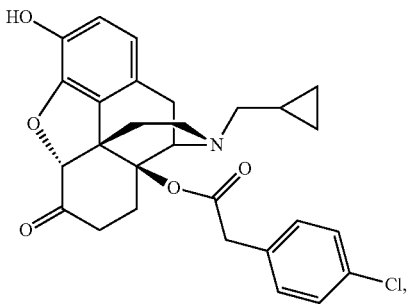
(9)
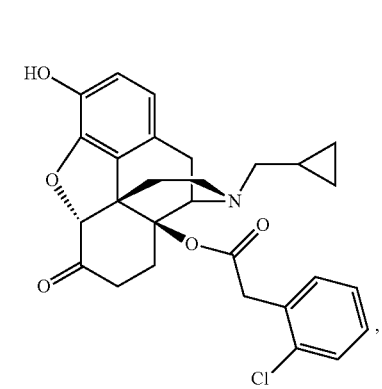
(10)
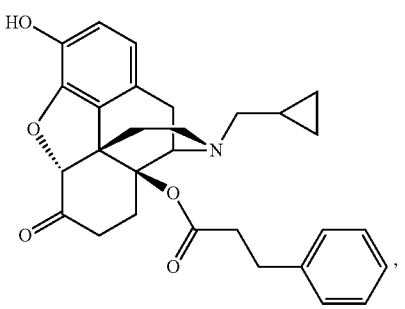
(11)
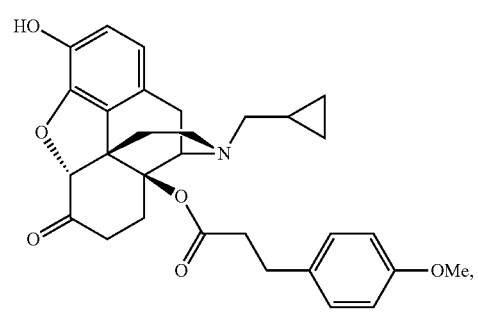
(12)
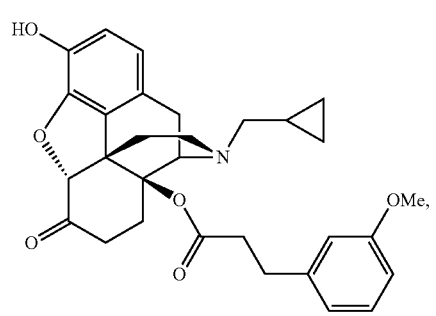
(13)

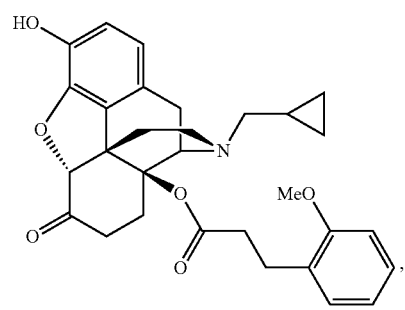
(14)
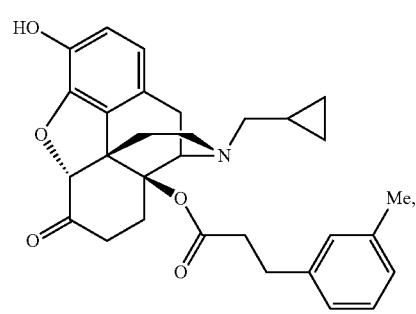
(15)
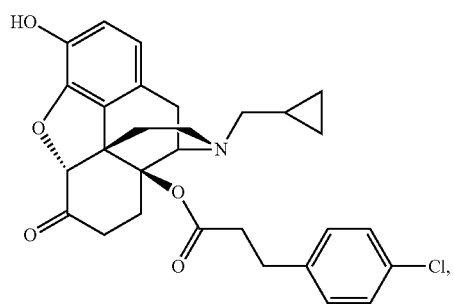
(16)
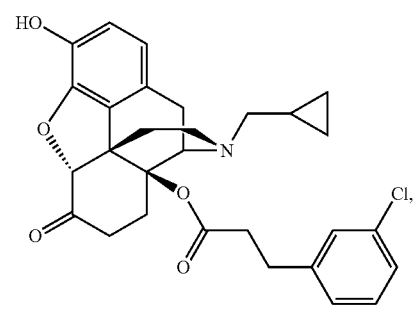
(17)
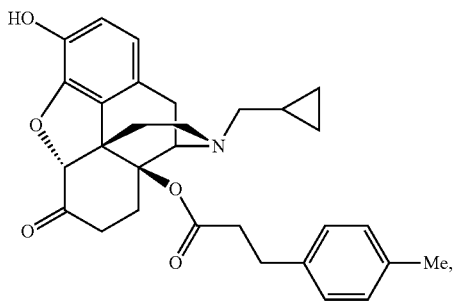
(18)
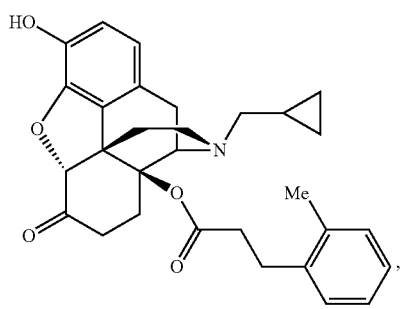
(19)
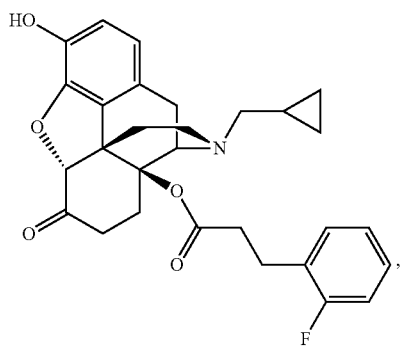
(20)
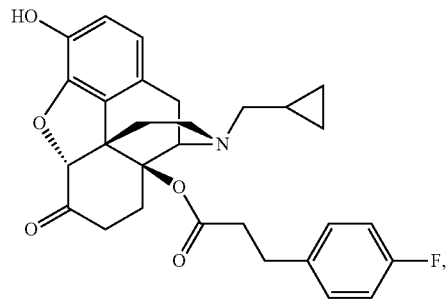
(21)
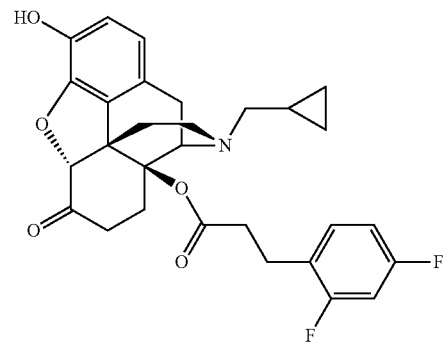
(22)
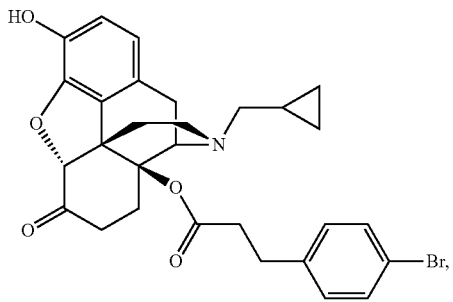
(23)

(24)
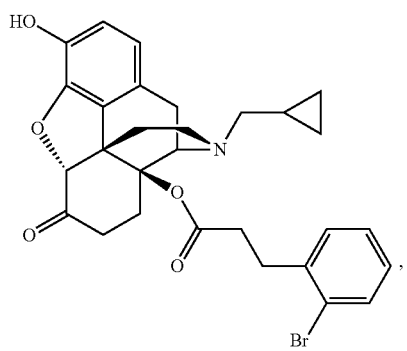
(25)
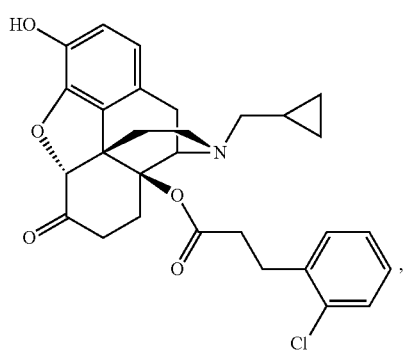
(26)
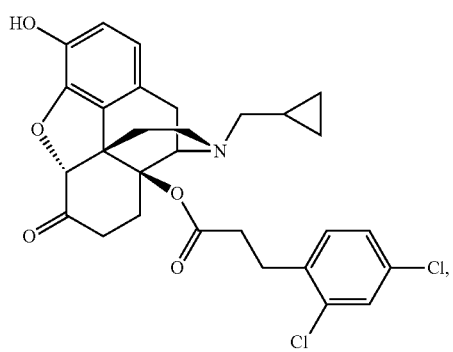
(27)
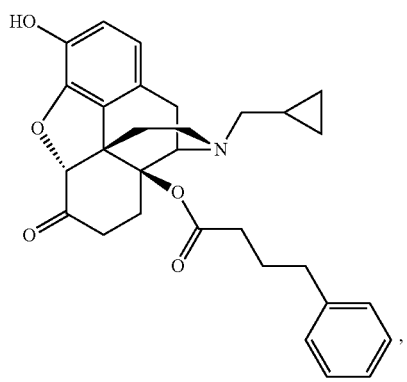
(28)
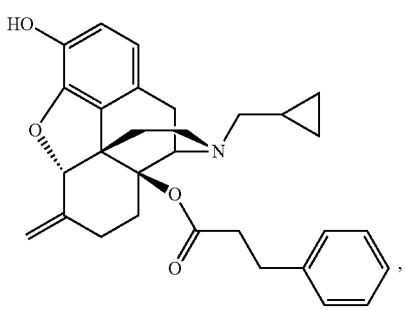
(29)
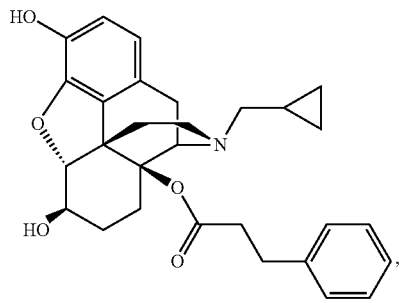
(30)
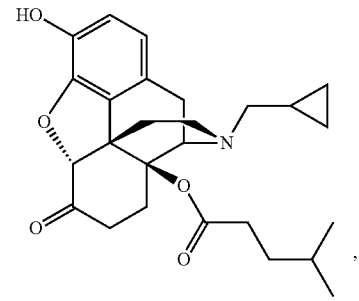
(31)
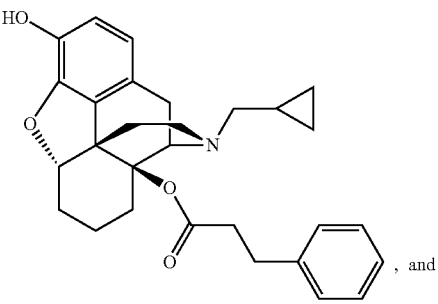
, and -continued

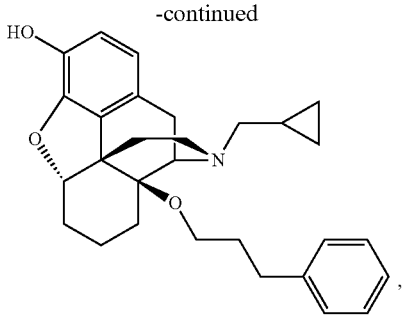

or a pharmaceutically acceptable salt thereof.

14. A compound selected from compounds of formula 2:

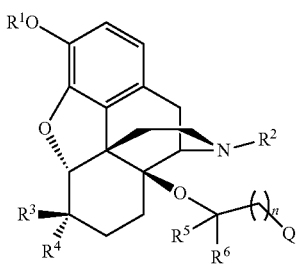

wherein:
R$^1$ is H or methyl;
R$^2$ is C$_{3-5}$ alkyl, C$_{3-5}$ alkenyl or C$_{3-5}$ cycloalkyl-C$_{1-2}$ alkyl;
R$^3$ and R$^4$ are together =CH$_2$;
R$^5$ and R$^6$ are together =O or both are H;
n is 1-4; and
Q is branched alkyl of 3-6 carbon atoms or branched alkenyl of 3-6 carbon atoms, phenyl, or heteroaryl of 5-6 ring atoms with at least one atom selected from N, O or S;
wherein said phenyl is substituted with one or two R$^Q$ substituents, and said heteroaryl is optionally substituted with one or two R$^Q$ substituents, wherein each R$^Q$ is independently selected from the groups consisting of halogen, C$_{1-3}$ alkyl, CF$_3$, OH, C$_{1-3}$ alkyloxy, —NH$_2$, —NHR$^7$, and NR$^7$R$^8$, wherein R$^7$ and R$^8$ are independently C$_{1-3}$ alkyl; or two adjacent R$^Q$ together form —O—(CH$_2$)$_m$—O—, wherein m is 1, 2 or 3;
with the proviso that when n is 1, Q is not unsubstituted phenyl
or a pharmaceutically acceptable salt, hydrate, and/or solvate thereof.

15. A compound selected from compounds of formula 2:

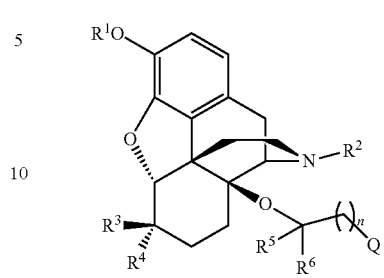

wherein:
R$^1$ is H or methyl;
R$^2$ is C$_{3-5}$ alkyl, C$_{3-5}$ alkenyl or C$_{3-5}$ cycloalkyl-C$_{1-2}$ alkyl;
one of R$^3$ and R$^4$ is H and the other is OH, or both are H;
R$^5$ and R$^6$ are both H;
n is 1-4; and
Q is branched alkyl of 3-6 carbon atoms or branched alkenyl of 3-6 carbon atoms, phenyl, or heteroaryl of 5-6 ring atoms with at least one atom selected from N, O or S;
wherein each phenyl or heteroaryl is optionally substituted with one or two R$^Q$ substituents, wherein each R$^Q$ is independently selected from the group consisting of halogen, C$_{1-3}$ alkyl, CF$_3$, OH, C$_{1-3}$ alkyloxy, —NH$_2$, —NHR$^7$, and NR$^7$R$^8$, wherein R$^7$ and R$^8$ are independently C$_{1-3}$ alkyl; or two adjacent R$^Q$ together form —O—(CH$_2$)$_m$—O—, wherein m is 1, 2 or 3.

16. A method for the treatment or prophylaxis of pain, the method comprising administering to a human or animal in need of such treatment or prophylaxis a therapeutically effective amount of a compound of any one of claim 1, 14, or 15.

17. The method of claim 16, wherein the method is for treatment or prophylaxis of neuropathic pain.

18. A pharmaceutical composition comprising an effective amount of a compound of any one of claim 1, 14, or 15 and a pharmaceutically acceptable carrier, diluent, or excipient.

19. A method of preparing the pharmaceutical composition of claim 18, the method comprising combining an effective amount of said compound with said pharmaceutically acceptable carrier, diluent, or excipient.

20. A method for the treatment or prophylaxis of pain, the method comprising administering, to a human or animal in need of such treatment or prophylaxis a therapeutically effective amount of a compound of claim 13.

21. The method of claim 20, wherein the method is for treatment or prophylaxis of neuropathic pain.

22. A pharmaceutical composition comprising an effective amount of a compound of claim 13 and a pharmaceutically acceptable carrier, diluent, or excipient.

23. A method of preparing the pharmaceutical composition of claim 22, the method comprising combining an effective amount of said compound with said pharmaceutically acceptable carrier, diluent, or excipient.

* * * * *